United States Patent
Bonneau et al.

(10) Patent No.: US 10,188,411 B2
(45) Date of Patent: Jan. 29, 2019

(54) EVERTING BALLOON FOR MEDICAL DEVICES

(71) Applicant: CALCULA TECHNOLOGIES, INC., San Francisco, CA (US)

(72) Inventors: Raymond Arthur Bonneau, San Francisco, CA (US); David Gal, San Francisco, CA (US); David Wellman Snow, San Carlos, CA (US)

(73) Assignee: CALCULA TECHNOLOGIES, INC., San Francisco, CA (US)

( * ) Notice: Subject to any disclaimer, the term of this patent is extended or adjusted under 35 U.S.C. 154(b) by 165 days.

(21) Appl. No.: 15/141,512

(22) Filed: Apr. 28, 2016

(65) Prior Publication Data
US 2016/0242799 A1    Aug. 25, 2016

Related U.S. Application Data

(63) Continuation-in-part of application No. 14/977,087, filed on Dec. 21, 2015, which is a continuation of
(Continued)

(51) Int. Cl.
*A61B 17/00*      (2006.01)
*A61B 1/05*      (2006.01)
(Continued)

(52) U.S. Cl.
CPC ........ *A61B 17/22032* (2013.01); *A61B 1/005* (2013.01); *A61B 1/05* (2013.01);
(Continued)

(58) Field of Classification Search
CPC ............ A61B 17/22032; A61B 17/221; A61B 17/2256; A61B 2017/2212;
(Continued)

(56) References Cited

U.S. PATENT DOCUMENTS 3,941,121 A    3/1976   Olinger et al.
4,243,040 A *   1/1981   Beecher ........... A61B 17/22032
                                                      604/271
(Continued)

FOREIGN PATENT DOCUMENTS

JP          10-118088      5/1998
WO    WO2008004238    1/2008

OTHER PUBLICATIONS

International Search Report, Korean Intellectual Property Office for PCT Application No. PCT/US2014/034284, dated Sep. 1, 2014, pp. 1-3.
Written Opinion of the International Searching Authority, Korean Intellectual Property Office for PCT Application No. PCT/US2014/034284, dated Sep. 1, 2014, pp. 1-9.
International Search Report Issued by the Korean Intellectual Property Office as the International Searching Authority for corresponding PCT Application No. PCT/US2014/068714, dated Mar. 18, 2015, pp. 1-3.
(Continued)

*Primary Examiner* — Martin T Ton
(74) *Attorney, Agent, or Firm* — Merchant & Gould P.C.

(57) ABSTRACT

A device for removing an obstruction from a lumen in a human or animal subject may include an inflatable balloon. The inflatable balloon may include a proximal tapered portion having a proximal taper angle, a central portion, and a distal tapered portion having a distal taper angle that is greater than the proximal taper angle. The balloon may also include at least one eversion feature on the proximal tapered portion and/or the distal tapered portion. The eversion feature may facilitate preferential eversion of the distal tapered portion into an inside of the balloon without the proximal tapered portion collapsing. Preferential eversion of the distal tapered portion may be provided by the differences in the distal and proximal taper angles and by one or more of a number of different types of eversion features.

14 Claims, 16 Drawing Sheets

Related U.S. Application Data application No. 14/205,026, filed on Mar. 11, 2014, now Pat. No. 9,232,956.

(60) Provisional application No. 61/897,769, filed on Oct. 30, 2013, provisional application No. 61/860,140, filed on Jul. 30, 2013, provisional application No. 61/812,511, filed on Apr. 16, 2013, provisional application No. 62/155,617, filed on May 1, 2015.

(51) Int. Cl.
| | | |
|---|---|---|
| *A61B 1/005* | (2006.01) | |
| *A61B 17/22* | (2006.01) | |
| *A61B 90/00* | (2016.01) | |
| *A61B 17/221* | (2006.01) | |
| *A61M 25/10* | (2013.01) | |
| *A61B 17/32* | (2006.01) | |

(52) U.S. Cl.
CPC ....... *A61B 17/221* (2013.01); *A61M 25/1034* (2013.01); *A61B 90/37* (2016.02); *A61B 2017/00526* (2013.01); *A61B 2017/2212* (2013.01); *A61B 2017/2215* (2013.01); *A61B 2017/22061* (2013.01); *A61B 2017/22068* (2013.01); *A61B 2017/320064* (2013.01); *A61B 2090/3614* (2016.02); *A61M 2025/109* (2013.01)

(58) Field of Classification Search
CPC ............ A61B 1/00163; A61B 1/00174; A61B 1/00177; A61B 1/00179; A61B 1/00181; A61B 1/00183; A61M 25/0021; A61M 25/0023; A61M 25/0067; A61M 25/0074; A61M 25/0082; A61M 2025/0004; A61M 2025/0006; A61M 2025/0079; A61M 2025/1068; A61M 2025/109; A61M 2025/1093
USPC .......... 606/127; 604/103.06, 103.07, 103.09, 604/103.14
See application file for complete search history.

(56) References Cited

U.S. PATENT DOCUMENTS

| | | |
|---|---|---|
| 4,469,100 A | 9/1984 | Hardwick |
| 4,590,938 A | 5/1986 | Segura |
| 4,611,594 A | 9/1986 | Grayhack |
| 4,815,816 A | 3/1989 | Schneider |
| 4,946,440 A | 8/1990 | Hall |
| 4,994,079 A | 2/1991 | Genese et al. |
| 5,057,114 A | 10/1991 | Wittich et al. |
| 5,159,920 A | 11/1992 | Condon |
| 5,163,927 A | 11/1992 | Woker et al. |
| 5,201,741 A | 4/1993 | Dulebohn |
| 5,311,858 A | 5/1994 | Adair |
| 5,364,345 A | 11/1994 | Lowery et al. |
| 5,630,797 A | 5/1997 | Diedrich et al. |
| 5,658,296 A | 8/1997 | Bates et al. |
| 5,944,728 A | 8/1999 | Bates |
| 6,059,796 A | 5/2000 | Bilitz et al. |
| 6,086,530 A | 7/2000 | Mack |
| 6,139,489 A | 10/2000 | Wampler et al. |
| 6,156,055 A | 12/2000 | Ravenscroft |
| 6,339,446 B1 | 1/2002 | Miyoshi |
| 6,448,545 B1 | 9/2002 | Chen |
| 6,554,765 B1 | 4/2003 | Yarush et al. |
| 6,692,484 B1 | 2/2004 | Karpiel et al. |
| 6,911,005 B2 | 6/2005 | Ouchi |
| 7,077,849 B2 | 7/2006 | Bates et al. |
| 7,201,770 B2 | 4/2007 | Johnson et al. |
| 7,654,989 B2 | 2/2010 | Knapp |
| 7,678,118 B2 | 3/2010 | Bates et al. |
| 7,731,723 B2 | 6/2010 | Kear et al. |
| 8,343,170 B2 | 1/2013 | Massicotte et al. |
| 8,444,661 B2 | 5/2013 | Nair et al. |
| 8,602,971 B2 | 12/2013 | Farr |
| 8,617,104 B2 | 12/2013 | Yribarren |
| 8,647,156 B2 | 2/2014 | Golko et al. |
| 8,858,535 B2 | 10/2014 | Riaz |
| 8,974,472 B2 | 3/2015 | Gal et al. |
| 9,033,865 B2 | 5/2015 | Suda |
| 9,232,956 B2 | 1/2016 | Bonneau et al. |
| 9,623,799 B2 | 4/2017 | Bingle et al. |
| 9,636,125 B2 | 5/2017 | Sepetka et al. |
| 9,642,637 B1 | 5/2017 | Lind et al. |
| 9,675,780 B2 | 6/2017 | Harari et al. |
| 9,743,944 B1 | 8/2017 | Bonneau et al. |
| 2001/0041899 A1 | 11/2001 | Foster |
| 2002/0026202 A1 | 2/2002 | Honey et al. |
| 2002/0068943 A1 | 6/2002 | Chu et al. |
| 2002/0068944 A1 | 6/2002 | White et al. |
| 2002/0072764 A1 | 6/2002 | Sepetka et al. |
| 2002/0095161 A1 | 7/2002 | Dhindsa |
| 2002/0133170 A1 | 9/2002 | Tsuruta |
| 2003/0004513 A1 | 1/2003 | Guzman et al. |
| 2003/0125606 A1 | 7/2003 | Amling |
| 2003/0195390 A1 | 10/2003 | Graumann |
| 2004/0097963 A1 | 5/2004 | Seddon |
| 2004/0138677 A1 | 7/2004 | Little et al. |
| 2004/0158261 A1 | 8/2004 | Vu |
| 2004/0201686 A1 | 10/2004 | Amling |
| 2005/0049613 A1 | 3/2005 | Brown |
| 2005/0070761 A1 | 3/2005 | Higuchi |
| 2005/0085826 A1 | 4/2005 | Nair et al. |
| 2005/0148842 A1 | 7/2005 | Wang et al. |
| 2005/0261705 A1* | 11/2005 | Gist .................. A61B 17/221 606/113 |
| 2005/0272975 A1 | 12/2005 | McWeeney |
| 2006/0020213 A1 | 1/2006 | Whitman et al. |
| 2006/0055793 A1 | 3/2006 | Adler |
| 2006/0173468 A1 | 8/2006 | Simmon et al. |
| 2006/0206007 A1 | 9/2006 | Bala |
| 2006/0209201 A1 | 9/2006 | Spears et al. |
| 2006/0271067 A1 | 11/2006 | Wolfe et al. |
| 2007/0038227 A1 | 2/2007 | Massicotte et al. |
| 2007/0048965 A1 | 3/2007 | Hsieh et al. |
| 2007/0093693 A1 | 4/2007 | Geist |
| 2007/0142771 A1* | 6/2007 | Durcan .................. A61F 2/958 604/103.06 |
| 2007/0299456 A1 | 12/2007 | Teague |
| 2008/0004485 A1* | 1/2008 | Moreschi ............ A61M 1/1075 600/16 |
| 2008/0188866 A1 | 8/2008 | Karpiel et al. |
| 2008/0246838 A1 | 10/2008 | Chatenever |
| 2008/0262359 A1 | 10/2008 | Tearney |
| 2009/0125037 A1 | 5/2009 | Goto |
| 2009/0237498 A1 | 9/2009 | Modell |
| 2009/0247828 A1 | 10/2009 | Watanabe |
| 2009/0253967 A1 | 10/2009 | Gill |
| 2009/0270907 A1* | 10/2009 | Todd ............... A61B 17/22031 606/198 |
| 2009/0287193 A1 | 11/2009 | Desai et al. |
| 2009/0318757 A1 | 12/2009 | Singh |
| 2010/0191050 A1 | 7/2010 | Zwolinski |
| 2010/0220179 A1 | 9/2010 | Wang |
| 2010/0261961 A1 | 10/2010 | Scott |
| 2011/0206381 A1 | 8/2011 | Ji et al. |
| 2011/0213381 A1 | 9/2011 | Leslie et al. |
| 2011/0275894 A1 | 11/2011 | Mackin |
| 2011/0275990 A1* | 11/2011 | Besser ............ A61B 17/22032 604/99.01 |
| 2012/0330350 A1 | 12/2012 | Jones |
| 2013/0018387 A1 | 1/2013 | Diamant |
| 2013/0077048 A1 | 3/2013 | Mirlay et al. |
| 2013/0096571 A1 | 4/2013 | Massicotte et al. |
| 2013/0165944 A1 | 6/2013 | Gal et al. |
| 2013/0204345 A1 | 8/2013 | Cully |
| 2013/0237879 A1 | 9/2013 | Takeuchi |
| 2013/0289578 A1 | 10/2013 | Noriega et al. |
| 2013/0303886 A1 | 11/2013 | Ludwin et al. |
| 2014/0012113 A1 | 1/2014 | Kaku et al. |

(56) References Cited

U.S. PATENT DOCUMENTS

| | | |
|---|---|---|
| 2014/0107496 A1 | 4/2014 | Hellstrom et al. |
| 2014/0309655 A1 | 10/2014 | Gal et al. |
| 2014/0309656 A1 | 10/2014 | Gal et al. |
| 2015/0119895 A1 | 4/2015 | Tah et al. |
| 2015/0133948 A1 | 5/2015 | Gal et al. |
| 2015/0282749 A1 | 10/2015 | Zand et al. |
| 2015/0305602 A1 | 10/2015 | Gal et al. |
| 2015/0305603 A1 | 10/2015 | Gal et al. |
| 2016/0106447 A1 | 4/2016 | Bonneau et al. |
| 2016/0235478 A1 | 8/2016 | Bonneau et al. |
| 2016/0242799 A1 | 8/2016 | Bonneau et al. |
| 2016/0345989 A1 | 12/2016 | Booker |
| 2016/0374702 A1 | 12/2016 | St. George et al. |
| 2018/0228505 A1 | 8/2018 | Bonneau et al. |
| 2018/0228545 A1 | 8/2018 | Bonneau et al. |
| 2018/0303499 A1 | 10/2018 | Bonneau et al. |

OTHER PUBLICATIONS

Written Opinion of the International Search Authority Issued by the Korean Intellectual Property Office as the International Searching Authority for corresponding PCT Application No. PCT/US2014/068714, dated Mar. 18, 2015, pp. 1-8.

Supplementary European Search Report for Application No. 14784589.5, dated Sep. 15, 2016, 6 pages.

International Search Report and Written Opinion for PCT/US2017/029914, dated Jul. 5, 2017, 17 pages.

International Search Report and Written Opinion for PCT/US2017/029925, dated Jul. 6, 2017, 11 pages.

* cited by examiner

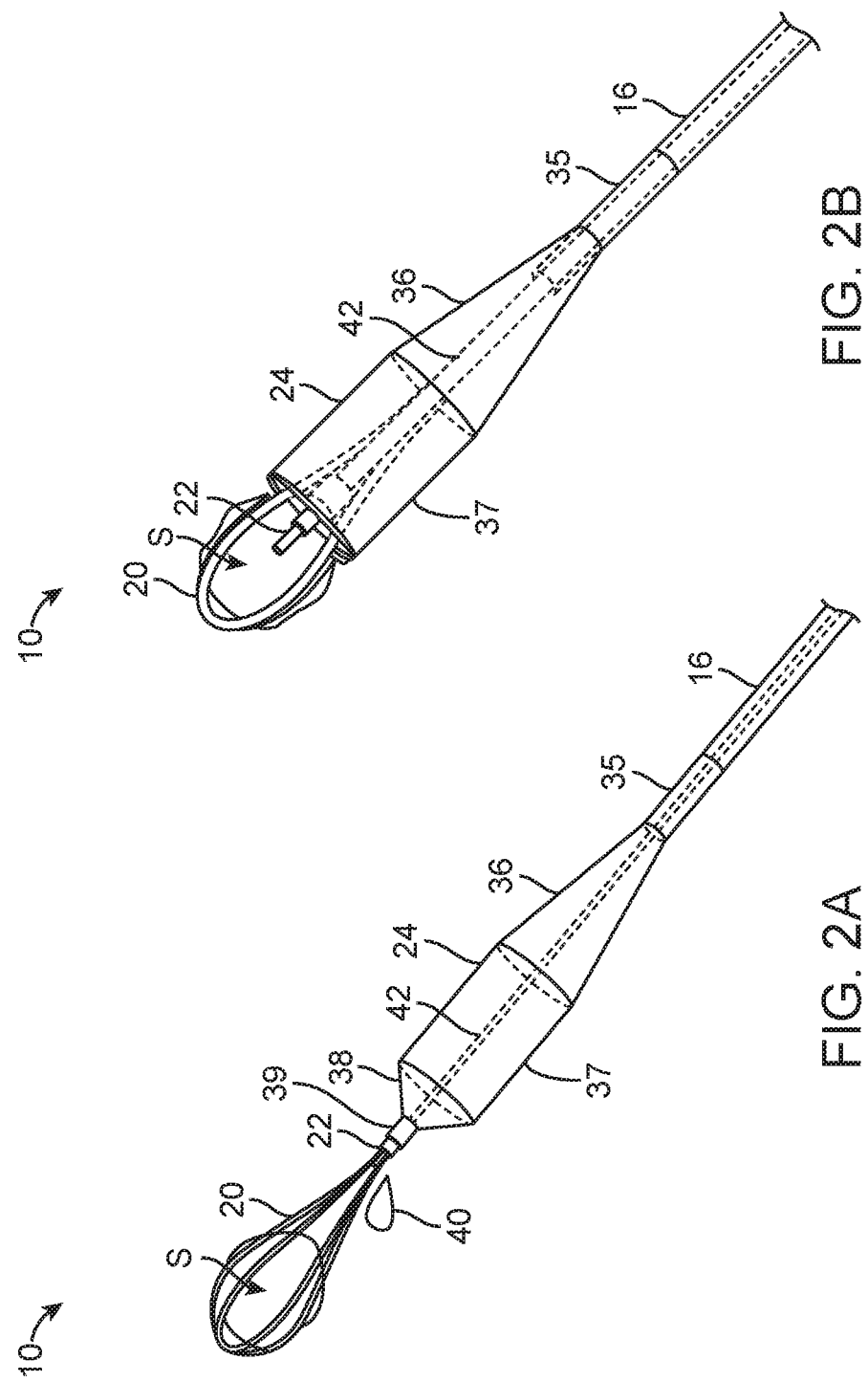

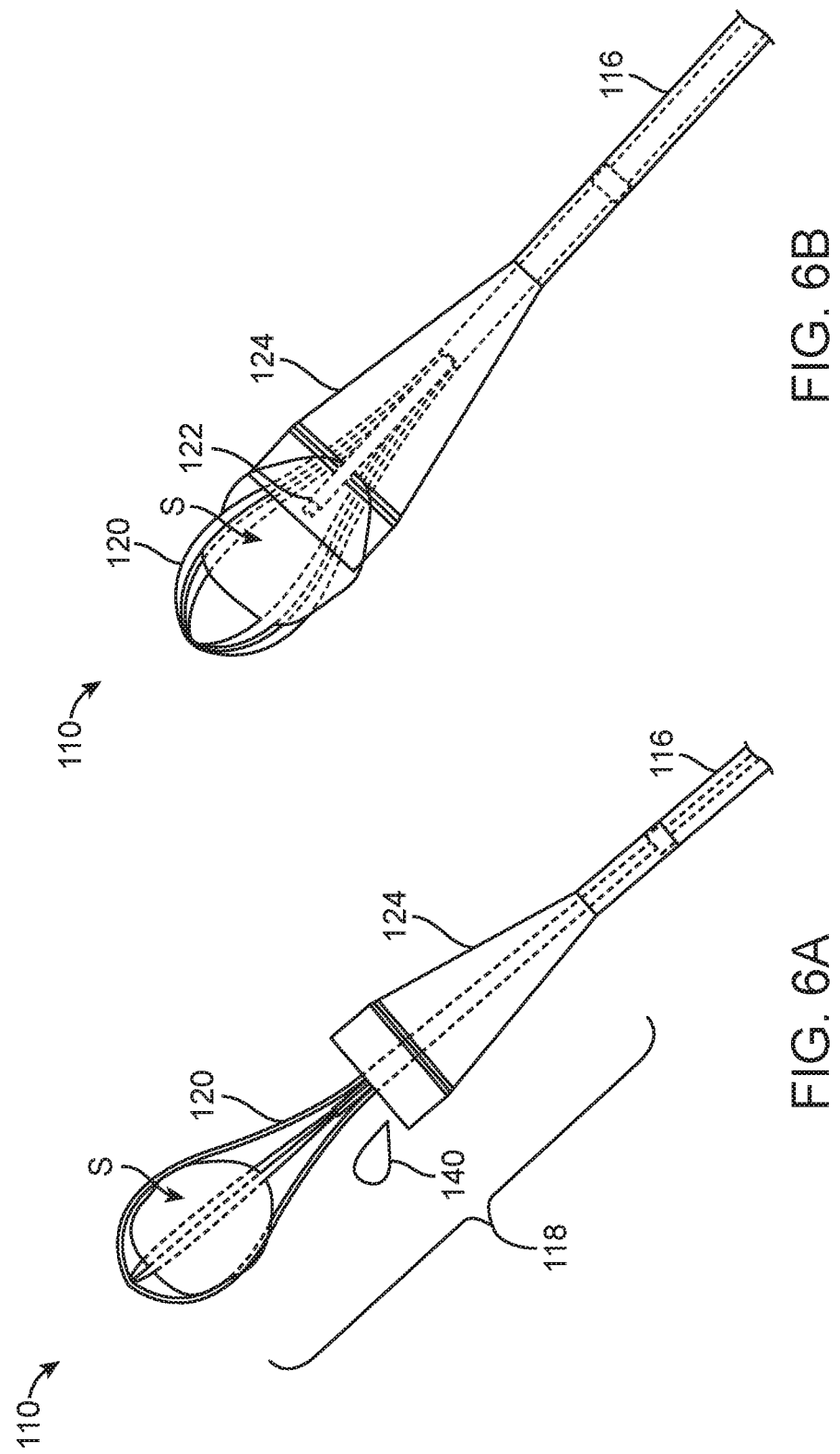

EVERTING BALLOON FOR MEDICAL DEVICES

CROSS-REFERENCE TO RELATED APPLICATIONS

This application is a continuation-in-part of U.S. patent application Ser. No. 14/977,087, filed Dec. 21, 2015, entitled "Devices for Removing Kidney Stones," which is a continuation of U.S. patent application Ser. No. 14/205,026, filed Mar. 11, 2014, entitled "Device for Removing Kidney Stones," which issued as U.S. Pat. No. 9,232,956 and claims priority to U.S. Provisional Application No. 61/897,769 filed Oct. 30, 2013, and 61/860,140 filed Jul. 30, 2013 and 61/812,511 filed Apr. 16, 2013. This application also claims priority to U.S. Provisional Application No. 62/155,617, filed May 1, 2015, entitled "Everting Balloon with Simplified Design and Control." The applications referenced above are herein incorporated fully by reference.

TECHNICAL FIELD

The present disclosure relates to medical devices and methods. More specifically, the disclosure relates to devices and methods for removing kidney stones.

BACKGROUND

Kidney stones (known as ureteral calculi in medical terminology) are a significant burden on society and the health care system. Kidney stones form in the body when the amount of various minerals in urine exceeds an amount that can be eliminated (the metastable limit), and the excess minerals form a precipitate. Most kidney stones are comprised of calcium and oxalate, though uric acid, struvite, cysteine, and other stone compositions are also commonly found.

Kidney stones typically form in the parts of the kidney known as the renal pelvis or calyces and can stay there for years. When a stone dislodges, it makes its way down the upper urinary tract towards the bladder. Stones often get stuck en route to the bladder in the ureter. One reason for this is that mechanical rubbing of the sharp stone on the ureter's mucosal lining causes an inflammatory response and swelling (or "edema"), which inhibits the stone's ability to pass. This obstruction impedes the passage of urine from the kidney to the bladder, which results in increased internal pressure in the kidney. This pressure rise causes nerve fibers in the kidney to stretch, which in turn results in the excruciating pain well known to accompany stones. Clinically, this pain is known as "renal colic" and comes in unexpected bursts lasting 2-18 hours, until the internal pressure of the kidney is reduced. As long as the stone remains in the urinary tract, a patient will be at risk for renal colic. Female patients describe stones as worse than natural childbirth, while male patients describe it as the most excruciating experience of their lives. The pain associated with kidney stones is not correlated with stone size. In fact, several urologists note that often the smaller stones are the ones that hurt the most, prompting the quotation, "Stones are like puppies, the smaller ones make the most noise."

Pain relief from kidney stones typically occurs instantly after stone passage or removal. Waiting for kidney stones to pass, however, can be a long and painful process. Currently, three general types of kidney stone removal methods are used, all of which have at least some shortcomings.

Extracorporeal Shockwave Lithotripsy (ESWL) is a procedure in which shockwaves are transmitted through the body in the direction of a kidney stone, in an attempt to fragment the stone into smaller pieces. For the ESWL procedure, a patient lies on a special bed (which costs approximately $750,000), is given sedation anesthesia, and is bombarded with 45-90 shocks per minute over the course of 45 minutes to one hour. The shocks are so intense that they must be synchronized with the patient's heartbeat so as not to cause cardiac arrhythmias. ESWL outcomes are mixed: 33% of patients have a successful outcome and pass "sand," 33% of patients pass several smaller stones with excruciating pain, and 33% of patients are unaffected by the treatment. Recent studies have raised concerns about potential long-term complications of ESWL, including hypertension and diabetes. Due to the uncertain outcomes, required sedation anesthesia, and potentially hazardous mechanism of the treatment, ESWL is indicated only for patients with 8-13 mm stones located in the kidney itself. Generally, stones of this size and location are asymptomatic.

Ureteroscopy (URS) is a procedure in which a urologist inserts an endoscope up the urethra, into the bladder, and up the ureter to the site of the stone. Using a laser, the urologist fragments the stone into smaller pieces and retracts the fragments with a basket. The procedure requires general anesthesia, high skill level from the urologist, and anywhere from 20 minutes to one hour. The endoscope, laser source, and fluoroscopy require an investment of approximately $225,000 in capital equipment alone. The ureteroscopes themselves cost approximately $15,000 and can typically be used in only about 15 procedures before needing to be replaced or repaired. The typical amount of manipulation of the ureteroscope within the ureter during the procedure, as well as the overall time spent in the ureter, can induce ureteral stricture (blockages of the ureter caused by a process similar to scarring). The procedure outcome is generally highly effective, but due to the risk of complications and required general anesthesia, URS is generally recommended only for stones that are 8-15 mm in size.

Percutaneous Nephrectomy Lithotripsy (PCNL) is a surgical procedure in which a tube is inserted through the back into the kidney. Stones are removed through the tube, using lasers, graspers, and aspiration. Though PCNL is highly effective, its invasiveness renders it applicable only to stones larger than 15 mm.

As described above, the currently available procedures for kidney stone removal are generally quite invasive and require (1) at least sedation anesthesia and in many cases general anesthesia, (2) expansive, specialized capital equipment, and (3) experienced and knowledgeable urologists to perform the procedures. Furthermore, most small kidney stones ultimately pass without any intervention. Therefore, despite the incredible, debilitating pain involved in passing kidney stones naturally, that is typically the method of choice, since kidney stone removal methods have such significant drawbacks.

Thus, it would be advantageous to have additional treatment options for kidney stone removal. Ideally, these options would be less invasive, less expensive, less prone to side effects, and/or require less physician expertise to perform. It would also be ideal if some of the additional treatment options could be used, or adapted for use, in other parts of the body to remove other obstructions. At least some of these objectives will be met by the embodiments described herein.

SUMMARY

This application describes a number of embodiments of devices, systems and methods for removing obstructions from body lumens and passageways. Although the embodiments are described primarily for use in removing kidney stones from the urinary tract, at least some of the embodiments may also be used, or may be adapted for use, in other parts of the body to remove other obstructions. Therefore, the following description should not be interpreted as limiting the scope of this application to kidney stone removal, since any embodiment described may be used or adapted for other uses. The terms "kidney stone," "stone" and "obstruction" may be used interchangeably herein. Additionally, although many of the descriptions below focus on removal of a kidney stone from the ureter, other parts of the body and/or other obstructions may be addressed in other embodiments. The terms "lumen" and "vessel," for example, may be used generally and interchangeably to refer to areas in which obstructions may be located.

Generally, this application describes devices, systems and methods for removing kidney stones from ureters (or other obstructions from other body lumens). In some embodiments, kidney stone removal may be performed without fragmenting the stones before removal. Alternatively, some embodiments may be used to remove fragmented stones. The various embodiments of devices, systems and methods described herein typically include one or more elongate, flexible shafts, arranged coaxially relative to one another, one or more end effectors at the distal end of the shaft(s) for removing the kidney stone, and a handle at the proximal end of the shaft(s) for manipulating the shaft(s) and end effector(s). It may be advantageous to include, in each embodiment, at least two of the following three aspects. It may be most advantageous to include all three aspects in a given embodiment, and some embodiments do include all three, but that is not required.

Obstruction retention. This refers to a mechanism for retaining or otherwise applying a force to the kidney stone or other obstruction for the purpose of retaining, manipulating and eventually removing the obstruction. Several examples of obstruction retention members described below include, but are not limited to, expandable graspers, expandable baskets and expandable balloons with cavities for trapping obstructions.

Ureter wall protection. This refers to a mechanism for protecting the ureteral wall (or wall of another lumen or vessel) from trauma caused by the stone or other obstruction rubbing against the wall during removal. In some but not all embodiments, ureter/vessel wall protection may involve ureteral/vessel dilation. Such embodiments may include a mechanism to provide dilation around the obstruction to reduce friction and eliminate trauma to the lumen wall caused by contact of the obstruction surface with the lumen wall. Generally, embodiments may involve any soft, compliant or low-friction material that may be positioned between the stone and the ureter wall. Several examples of ureter wall protection members described below include, but are not limited to, expandable balloons, shafts, and hydrodilation members that emit fluid to expand the ureter/vessel/lumen.

Obstruction detection and/or identification. This refers to a mechanism to identify the obstruction location and ensure retention and/or dilation is applied in the proper location relative to the obstruction. Detection may also be used to ensure removal of the stone and for general navigational purposes in the lumen or other orifice. One example of an obstruction detection member described below includes, but is not limited to, a fiber optic camera incorporated into an obstruction removal device.

Many of the embodiments of devices, systems and methods described below may include one mechanism from each of the three categories above-obstruction retention, ureter wall protection and obstruction detection. This combination may be advantageous in providing for effective kidney stone removal with minimal trauma to the ureter. In many embodiments, it will be possible to combine different mechanisms from one category with different mechanisms from another category to form an alternative embodiment. For clarity, the descriptions below will not always repeat details about various mechanisms from each category for each embodiment. For example, if a fiber optic camera is described in relation to one embodiment as a stone detection mechanism, that same camera need not be described again in detail for use with another embodiment. Mechanisms from each of the three categories may be combined with each other in any suitable way to form various alternative embodiments.

A number of the embodiments described herein include an inflatable balloon at or near a distal end of a stone removal device. The balloon is used primarily for ureter wall protection, with the stone being pulled back into the balloon before removal and/or the balloon being advanced over and around the stone before removal. The balloon may also help with the obstruction retention function of the device, helping to hold the stone within the device for removal. The balloons described herein may be referred to as everting balloons, and such balloons have a number of medical applications, not simply for use in ureteral stone removal devices. For example, everting balloons are sometimes used in devices and methods for tissue and cell collection, stent deployment, obstruction retention, vessel wall protection, and vessel dilation, among others. Although there are a number of differences between the everting balloons used for different medical applications, most if not all everting medical device balloons would benefit from a consistent and predictable balloon eversion. Everting balloons for medical devices have been described previously, such as in U.S. Patent Pub. No. 2013/0204345 and U.S. Pat. No. 7,201,770. These references, however, do not describe or suggest how to construct an everting balloon with consistent and predictable everting motion.

In one aspect, a system for removing a kidney stone from a ureter may include: an elongate, flexible, outer shaft, having a distal end configured to be advanced into the ureter and a proximal end; an elongate, flexible, inner shaft extending through at least part of the outer shaft, where at least one of the outer shaft or the inner shaft is moveable along a longitudinal axis relative to the other shaft; an expandable stone retention member extending through at least part of the inner shaft and moveable along the longitudinal axis relative to the inner shaft, where the stone retention member includes a retention member shaft and a stone retention portion disposed at a distal end of the retention member shaft; an elongate, flexible camera positioned coaxially within the retention member shaft, such that a distal end of the camera is located at or near a distal end of the inner shaft; and a handle coupled with the proximal end of the outer shaft, a proximal end of the inner shaft, and a proximal end of the retention member shaft. The handle may include a shaft actuator for moving the inner shaft relative to the outer shaft and/or the outer shaft relative to the inner shaft and a retention member actuator for advancing the stone retention member out of the distal end of the inner shaft.

Some embodiments may further include a compliant ureter wall protection member attached to the outer shaft at or near its distal end. Such embodiments may also optionally include a wall protection member shaft disposed between the outer shaft and the inner shaft, where a first end of the wall protection member is coupled with the distal end of the outer shaft, and a second end of the wall protection member is coupled with a distal end of the wall protection member shaft. In one embodiment, the wall protection member may be an inflatable balloon, and a space between the outer shaft and the wall protection member shaft may act as an inflation lumen in fluid communication with the balloon. In such embodiments, the handle may further include a balloon inflation port in fluid communication with the inflation lumen. In one embodiment, the balloon may be configured to at least partially deflate automatically when the stone retention member and a retained stone are pulled into the balloon. In one embodiment, the balloon inflation port may be configured to attach to a syringe, and automatic deflation of the balloon may cause a plunger of the syringe to automatically retract.

In some embodiments, the balloon may have a proximal taper with a first taper angle and a distal taper with a second taper angle that is greater than the first taper angle. Optionally, the wall protection member shaft may be movable along the longitudinal axis relative to the outer shaft, such that sliding the wall protection member proximally relative to the outer shaft causes the wall protection member to invaginate. In some embodiments, the system may further include a wall protection member shaft actuator on the handle.

Optionally, the handle may further include a handle extension, which is a portion of the handle that slides in and out of the distal end of the main portion of the handle—e.g., the larger, more proximal portion. Such a handle extension may be attached to any one or more components of the system, so that as the extension slides in and out of the handle, the attached component(s) move with the extension. Alternatively or additionally, the handle extension may include one or more other features. For example, the handle extension may be attached to a proximal end of an outer shaft of the system, and in some embodiments the distal end of the outer shaft may be attached to a wall protection member, such as an inflatable balloon. Moving the handle extension may thus move the outer shaft and change the configuration of the balloon. Examples of other features of a handle extension may include, but are not limited to, an inflation fluid port and an irrigation fluid port. The handle extension is an optional feature and may be referred to simply as a sliding handle piece or a moveable part of the handle. In various alternative embodiments, any feature(s) described as residing on the handle extension may instead by housed on the more proximal, main part of the handle.

The system may also optionally include at least one irrigation fluid channel and/or aperture in the inner shaft, in the wall protection member, in a space between the inner shaft and the retention member shaft, or in any other suitable location, for allowing passage of irrigation fluid out of the system. In these embodiments, the handle may further include an irrigation port. In one embodiment, for example, an irrigation port is in fluid communication with a space between the inner shaft and the retention member shaft, and that space acts as an irrigation fluid channel. In one embodiment, the stone retention portion of the stone retention member may be an expandable basket. In various embodiments, the camera may be a fiber optic camera, a CCD image sensor, a CMOS device or the like. The camera may optionally be removable from the system, in some embodiments. In some embodiments, the system may also include an inflation device attachable to the handle for inflating a ureter wall protection balloon coupled with the outer shaft and an irrigation fluid delivery device attachable to the handle for providing irrigation fluid during removal of a kidney stone. In some embodiments, the inflation device may be a syringe. Optionally, the system may further include a suction port on the handle for providing suction force through at least one of the inner shaft or the retention member shaft.

In another aspect, a device for removing a kidney stone from a ureter may include: an elongate, flexible, outer shaft having a distal end configured to be advanced into the ureter and a proximal end; an elongate, flexible, inner shaft extending through at least part of the outer shaft, where at least one of the outer shaft or the inner shaft is moveable along a longitudinal axis relative to the other shaft; an expandable stone retention member extending through at least part of the inner shaft and moveable along the longitudinal axis relative to the inner shaft, where the stone retention member includes a retention member shaft having a distal end and stone retention portion disposed at its distal end, and where the retention member shaft forms a camera lumen configured to allow a flexible camera to be positioned coaxially within it; and a handle coupled with the proximal end of the outer shaft, a proximal end of the inner shaft, and a proximal end of the retention member shaft. The handle may include a shaft actuator for moving the inner shaft relative to the outer shaft and/or the outer shaft relative to the inner shaft and a retention member actuator for advancing the stone retention member out of the inner shaft distal end.

In some embodiments, the handle may further include a camera attachment portion for attaching a proximal portion of the camera. Optionally, the device may further include a wall protection member coupled with the distal end of the outer shaft. Such an embodiment may also include a wall protection member shaft slidably disposed between the inner shaft and the outer shaft, where the wall protection member is attached at one end to the distal end of the outer shaft and at an opposite end to a distal end of the wall protection member shaft. In some embodiments, the wall protection member may be an inflatable balloon, and a space between the wall protection member shaft and the outer shaft may serve as an inflation lumen in fluid communication with the balloon. In such embodiments, the handle may optionally further include a balloon inflation port in fluid communication with the inflation lumen.

The device may also include an irrigation fluid channel formed as a space between the inner shaft and the retention member shaft. Such an embodiment may also include an irrigation fluid port on the handle in fluid communication with the irrigation channel. Although suction is not required in any embodiment, one optional feature of the device may be a suction port on the handle for providing suction force through the inner shaft and/or the retention member shaft.

In another aspect, a method for removing a kidney stone from a ureter may involve: advancing a distal end of an elongate, flexible kidney stone removal device into the ureter to a location near the kidney stone; advancing an expandable stone retention member out of an inner shaft of the device; visualizing at least part of the stone retention member with a camera disposed coaxially within the stone retention member; trapping the kidney stone in the stone retention member; surrounding at least a portion of the stone retention member and the trapped kidney stone with a wall protection member on the distal end of the kidney stone removal device; and removing the kidney stone removal device from the ureter while the stone retention member and the kidney stone are at least partially surrounded by the wall protection member.

In some embodiments, the retention member may include a retention member shaft and a stone retention portion disposed at a distal end of the retention member shaft, and the camera may be disposed in the retention member shaft such that a distal end of the camera is located at or near the distal end of the inner shaft. In some embodiments, the surrounding step may involve pulling the stone retention member and the trapped kidney stone proximally into the wall protection member. Alternatively, the surrounding step may involve advancing the wall protection member around at least part of the stone retention member and the trapped kidney stone.

In some embodiments, the wall protection member may be an inflatable balloon, and the method may further involve inflating the balloon. In such embodiments, surrounding at least part of the stone retention member and the trapped kidney stone may invaginate the balloon. In some embodiments, the surrounding step may automatically partially deflate the balloon and thus cause a plunger of an inflation syringe used to inflate the balloon to retract. In some embodiments, the balloon may be inflated after trapping the kidney stone. The method may optionally further include inflating the balloon at least one additional time during removal of the device from the ureter. Additionally, the method may also optionally include at least partially deflating the balloon at least one time before or during removal of the device from the ureter. These inflations and deflations may be performed, for example, to dilate a stricture or narrowing of the ureter.

Another optional step of the method is passing irrigation fluid, lubrication fluid and/or anesthetic out of the kidney stone removal device in an area near the kidney stone. In some cases, one fluid may be used for multiple purposes, such as irrigation to maintain a clear field of view for the camera, lubrication for facilitation stone removal, and/or anesthesia for reducing pain. A solution including lidocaine, for example, may achieve these purposes. In some embodiments, the method may also involve applying suction force through the device to help retain the kidney stone within the device. However, application of suction is not required as part of the method. Removing the camera from the device after use is yet another optional step. In some embodiments, the camera may be reusable for multiple kidney stone removal procedures. In such cases, the camera will be sterilizable by at least one sterilization method.

The method may also include, before the trapping step, advancing the inner shaft around the kidney stone and advancing an expandable, stone retention portion of the stone retention member out of the inner shaft. In one embodiment, trapping the stone comprises pulling back the stone retention member to trap the stone in the stone retention portion. In some embodiments, the surrounding step may involve pulling back the inner shaft to thus pull back the retained stone and the stone retention portion into the wall protection member. Any embodiments may further involve visualizing the trapping, surrounding and/or removing steps, using the camera.

In another aspect, a device for removing an obstruction from a lumen in a human or animal subject may include: a handle; a shaft slider coupled with the handle; a retention member slider coupled with the handle and configured to slide back and forth along the handle independently from the shaft slider; an elongate, flexible, outer shaft, having a distal end configured to be advanced into the ureter and a proximal end fixedly attached to the shaft slider, where the outer shaft defines a longitudinal axis; a lumen wall protection member shaft coaxially disposed within the outer shaft; an inflatable balloon; and an expandable obstruction retention member extending coaxially within the lumen wall protection member shaft and attached proximally to the retention member slider. The inflatable balloon may include: a proximal attachment portion coupled with the distal end of the outer shaft; a proximal tapered portion having a proximal taper angle relative to the longitudinal axis; a central portion; a distal tapered portion having a distal taper angle relative to the longitudinal axis that is greater than the proximal taper angle; a distal attachment portion coupled with a distal end of the lumen wall protection member shaft; and at least one eversion feature on the proximal tapered portion and/or the distal tapered portion. The eversion feature is configured to facilitate preferential eversion of the distal tapered portion into an inside of the balloon without the proximal tapered portion collapsing. Furthermore, a space between the outer shaft and the lumen wall protection member shaft forms an inflation lumen in fluid communication with the inflatable balloon.

In some embodiments, the proximal taper angle is between about 5 degrees and about 25 degrees, and the distal taper angle is between about 30 degrees and about 90 degrees. In some embodiments, the eversion feature may be a greater thickness of material on the proximal tapered portion as compared to the distal tapered portion. In some embodiments, the eversion feature may be a higher durometer material on the proximal tapered portion as compared to the distal tapered portion. In some embodiments, the eversion feature may be at least one extra layer of material on the proximal tapered portion as compared to the distal tapered portion. In some embodiments, the eversion feature may be feature comprises multiple support ribs on the proximal tapered portion. In various embodiments, the balloon may include any combination of these features and/or other features described herein.

In some embodiments, the balloon is configured to automatically deflate at least partially, and the distal tapered portion is configured to automatically evert into the inside of the balloon, when the obstruction is pulled into the distal tapered portion or the balloon is advanced over the obstruction. In some embodiments, the device may include an inflation device. In some embodiments, the lumen wall protection member shaft is movable along the longitudinal axis relative to the outer shaft, and sliding the wall protection member shaft proximally relative to the outer shaft causes the distal tapered portion to evert into the balloon.

The obstruction retention member may include: a retention member shaft forming a lumen and having a proximal end fixedly attached to the retention member slider, such that when the retention member slider slides back and forth along the handle, the retention member shaft slides with the retention member slider; and an expandable basket disposed at a distal end of the retention member shaft. Optionally, the device may also include an elongate, flexible, inner shaft extending coaxially within at least part of the lumen wall protection member shaft and having a proximal end fixedly attached to the handle, wherein the obstruction retention member is disposed coaxially within the inner shaft. Also optionally, the device may further include an elongate, flexible camera positioned coaxially within the lumen of the retention member shaft, wherein a proximal end of the camera is fixedly attached to the handle, such that the camera does not move relative to the handle and the inner shaft, and such that a distal end of the camera is located at or near a distal end of the inner shaft, where the retention member shaft slides back and forth between the inner shaft and the camera.

In another aspect, a method for manufacturing a catheter device for removing an obstruction from a lumen in a human or animal subject may involve: manufacturing a catheter shaft portion of the catheter device, the catheter portion having an inner shaft and an outer shaft; manufacturing an inflatable balloon; forming at least one eversion feature on at least one of the proximal tapered portion or the distal tapered portion of the inflatable balloon, where the at least one eversion feature is configured to facilitate preferential eversion of the distal tapered portion into an inside of the balloon without the proximal tapered portion collapsing; and attaching the inflatable balloon to the catheter shaft portion. As mentioned above, the inflatable balloon may be manufactured to include: a proximal attachment portion configured to be coupled with the distal end of the outer shaft; a proximal tapered portion having a proximal taper angle relative to the longitudinal axis; a central portion; a distal tapered portion having a distal taper angle relative to the longitudinal axis that is greater than the proximal taper angle; and a distal attachment portion configured to be coupled with a distal end of the inner shaft.

In some embodiments, forming the eversion feature may involve forming the proximal tapered portion with a greater thickness of material than the distal tapered portion. In some embodiments, forming the eversion feature may involve dipping the proximal tapered portion in a balloon material for a larger number of times and/or a larger amount of time than the distal tapered portion is dipped. In some embodiments, forming the eversion feature may involve forming the proximal tapered portion with a higher durometer material than the distal tapered portion. In some embodiments, forming the eversion feature may involve forming the proximal tapered portion with at least one extra layer of material than on the distal tapered portion. In some embodiments, forming the eversion feature may involve forming multiple support ribs on the proximal tapered portion. In one embodiment, forming the multiple support ribs may involve manufacturing the balloon on a mandrel having multiple cutout portions corresponding to the support ribs. In some embodiments, the method may further involve, after attaching the inflatable balloon to the catheter shaft portion, inflating and deflating the balloon at least one time, while applying a force to at least part of the balloon to facilitate eversion of the distal tapered portion while maintaining a shape of the proximal tapered portion without collapsing. Any of these manufacturing techniques may combined in one manufacturing method, according to various embodiments.

These and other aspects and embodiments will be described in further detail below, in reference to the attached drawing figures.

BRIEF DESCRIPTION OF THE DRAWINGS

FIGS. 2A and 2B are perspective views of a distal portion of the system of FIGS. 1A and 1B, illustrating further details of the system and a portion of a method for retaining a kidney stone in the system, according to one embodiment;

FIGS. 6A and 6B are perspective views of a distal portion of a kidney stone removal system having an expandable basket and a funnel member, according to an alternative embodiment;

DETAILED DESCRIPTION

The following description outlines various embodiments of devices, systems and methods for removing obstructions from body lumens in human or animal subjects. One example of such an obstruction is a kidney stones in a ureters. Although the following descriptions focus on kidney stone removal applications, some or all of the aspects and embodiments described below may alternatively be used in other body lumens for removal of other obstructions. Therefore, the scope of the invention extends beyond devices, systems and methods for removing kidney stones and should not be interpreted as being limited to that clinical application.

As mentioned above, the various embodiments described herein typically include at least two and sometimes three of the following: an obstruction retention member, a vessel/ lumen wall protection member, and an obstruction detection and/or identification member. Some descriptions below are directed to only one or two of these components, while other descriptions relate to embodiments of devices, systems or methods including all three components. Alternative embodiments, some of which may not be described below, may include various alternative combinations of the components described below in relation to other embodiments. In various alternative embodiments, the devices, systems and methods may be altered, combined or otherwise changed, without departing from the scope of the invention as set forth in the claims.

Figure 1A:
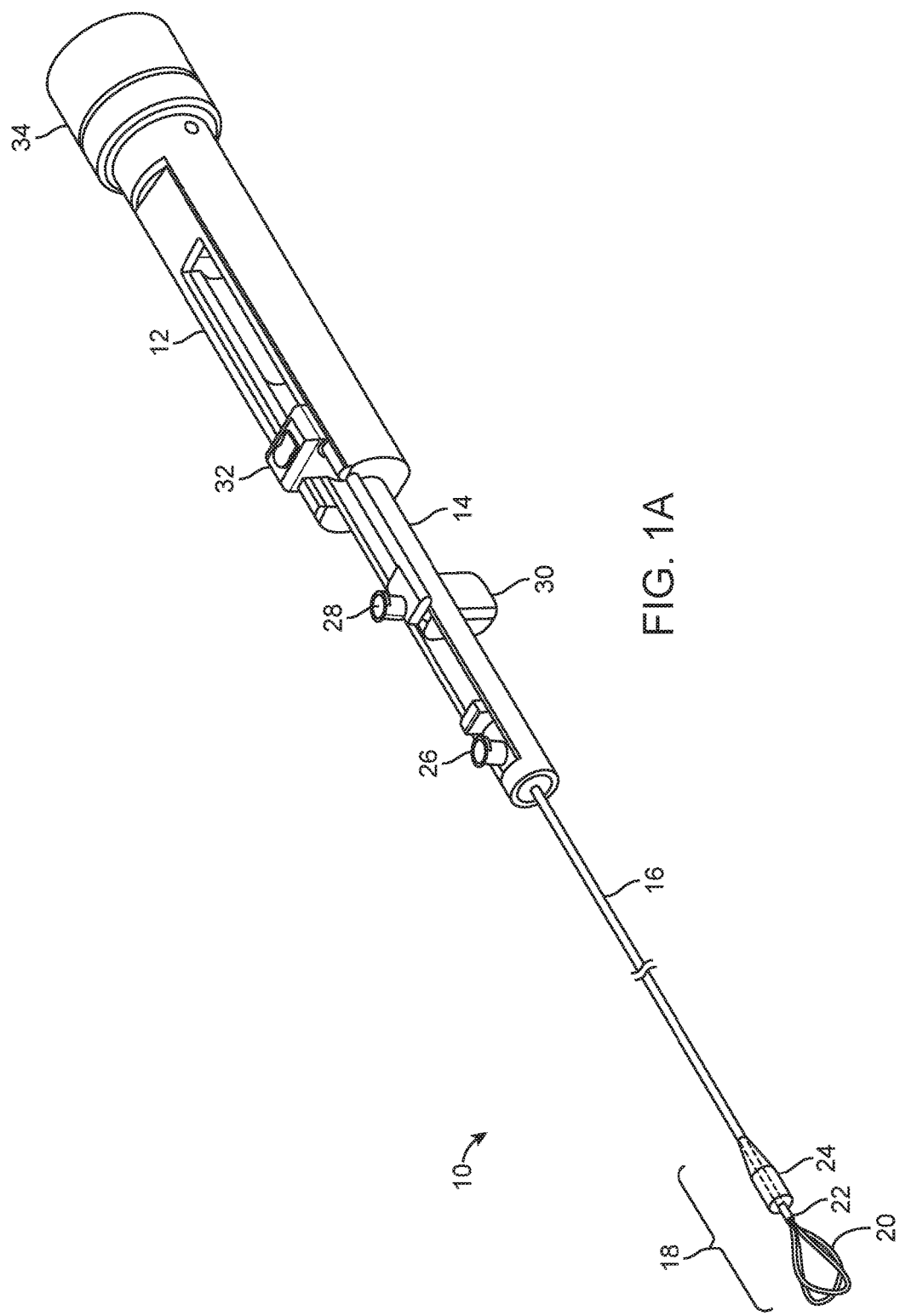
FIGS. 1A and 1B are perspective and side views, respectively, of a system for removing kidney stones from ureters or other obstructions from other body lumens, according to one embodiment.
Figure 1B:
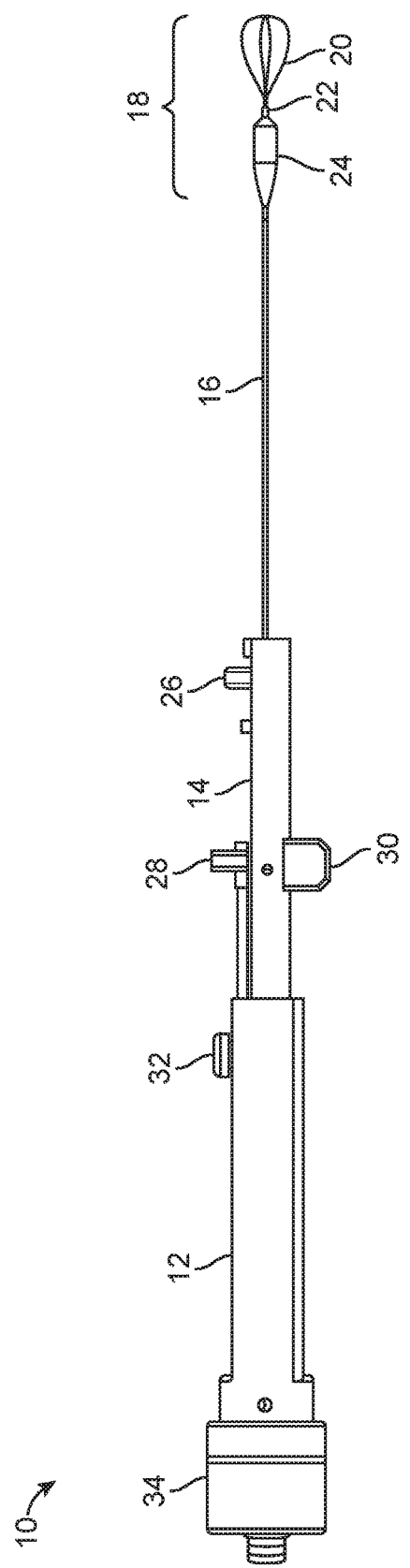

Referring to FIGS. 1A-1B, in one embodiment, a kidney stone removal system 10 may include a handle 12, a handle extension 14, an outer shaft 16 and an end effector 18. In one embodiment, end effector 18 may include an expandable stone retention member 20 (also referred to in this embodiment as "basket 20"), a visualization device 22 (also referred to in this embodiment as "camera 22"), and a wall protection member 24 (also referred to in this embodiment as "inflatable balloon 24"). Handle extension 14, as mentioned above, is simply a sliding portion of handle 12, which slides out of and back into the distal end of handle 12. It is an optional feature. In this embodiment, handle extension 14 is coupled with a balloon fill port 26, an irrigation port 28 and a shaft slider 30. Handle 12 may include a retention member slider 32 and may be coupled with a camera proximal portion 34, which may include an imaging sensor (and electronics) and/or a light source in some embodiments. Many of these features are described in further detail below.

In various embodiments, end effector 18 may include a number of variations, such as different components, differently sized components, and the like. For ease of description, end effector 18 is referred to here as a distal portion of system 10, which includes multiple different kidney stone removal components. Alternatively, the term "end effector" may be used elsewhere herein to refer to one component at or near the distal end of system 10. In the embodiment illustrated in FIGS. 1A and 1B, end effector 18 includes stone retention member 20, which includes a retention member shaft (not visible in FIGS. 1A and 1B) and an expandable, stone retention portion extending distally from a distal end of the retention member shaft. In this embodiment, the stone retention portion is an expandable basket. Again, the terms "stone retention member 20" and "basket 20" may be used interchangeably herein, although the stone retention member may comprise a one-piece or attached retention member shaft and expandable stone retention portion. In alternative embodiments, the stone retention portion of stone retention member 20 may be something other than an expandable basket, such as an expandable cup, tongs or the like.

Basket 20 may be made of Nitinol, spring stainless steel, shape memory polymer, or any other suitable shape-memory material. Basket 20 may be an extension of (or alternatively attached to) a distal end of the retention member shaft, which may be disposed within an inner shaft (not visible in FIGS. 1A and 1B). The inner shaft, in turn, is located within outer shaft 16. The various relationships of the shafts, according to at least one embodiment, are described in further detail below, in relation to FIGS. 3A and 3B. Generally, basket 20 is housed within the inner shaft during advancement of shaft 16 into and through the ureter. Basket 20 is then advanced distally out of the inner shaft to be released from constraint. Upon release from constraint, basket 20 expands and may then be used to trap a kidney stone. Basket 20 may include any suitable number of struts, such as but not limited to the four struts illustrated in FIGS. 1A and 1B.

In some embodiments, end effector 18 may also include visualization device 22 (or "camera 22") for detection and visualization of kidney stones. Visualization device 22 refers generally to the entire device used in system 10 for visualization and not just the distal tip of device 22 that is illustrated in FIGS. 1A and 1B. For example, camera 22 typically extends from a distal end, located at or near a distal end of the inner shaft, through the inner shaft, to camera proximal portion 34, which is attached to handle 12. Camera 22 may be any suitable small camera, such as but not limited to a fiber optic camera, a CCD (charge-coupled device) image sensor or a CMOS (complementary metal-oxide-semiconductor) camera. Camera proximal portion 34 may be attached via a cable with one or more conductors to an image-processing console (not shown), which displays an image on a viewing screen. Alternatively, camera proximal portion 34 may contain an eyepiece, through which an image may be observed and/or magnified using other techniques common in the art of endoscopy. The distal, viewing end of camera 22 is located in end effector 18, so that it may be used to visualize a kidney stone located in the ureter in front of system 10. In some embodiments, camera 22 is located coaxially within the retention member shaft (again, not shown in FIGS. 1A and 1B but illustrated later), with its distal end positioned at or near a distal end of the inner shaft and/or the retention member shaft. The retention member shaft extends distally to form basket 20, and the distal tip of camera 22, in these embodiments, generally faces directly into the expandable portion of basket 20.

In some embodiments, the distal end of camera 22 may be fixed in place, relative to the distal tip of the inner shaft. Camera 22 extends from its distal end, proximally through the retention member shaft to camera proximal portion 34, which is coupled with handle 12. In various embodiments of system 10, any suitable camera 22 currently available or as yet to be invented may be used. Furthermore, although visualization device 22 is referred to herein as a "camera," any other suitable visualization device may be used in alternative embodiments. In some embodiments, system 10 may include camera 22, while in other embodiments, system 10 may be provided without camera 22, and any of a number of available cameras may be added to system 10.

Finally, end effector 18 may also include wall protection member 24, also referred to as inflatable balloon 24, which is used both for protecting the ureteral wall from trauma and also to aid in stone retention. In alternative embodiments, some of which are described below, wall protection member 24 may be something other than an inflatable balloon, such as a compliant cup or other form of compliant material. Thus, use of the term "balloon" in describing the present embodiment should not be interpreted as limiting. Balloon 24 may also be used to help maintain a position of system 10 relative to the ureter, once it is inflated. Additionally, balloon 24 may be used during advancement or withdrawal of system 10 into or out of the ureter, to expand a portion of the ureter, for example to expand a constriction or other narrowing of the ureter. Balloon 24 may be made of any suitable polymer, polymeric blend or other material or combination of materials. Generally, such material(s) will be relatively atraumatic to the ureteral wall and ideally will have a low-friction and/or hydrophilic outer surface or coating that facilitates sliding along the wall. In some embodiments, balloon 24 may be coated with a lubricious coating and/or may include one or more small holes for allowing a lubricating fluid to escape.

As will be described in further detail below, in one embodiment, end effector 18 may be advanced through the ureter to a location near the kidney stone. The small, inner shaft, containing basket 20, may be extended out of outer shaft 16 during all, or at least part of, this advancement, and the whole device may be advanced until a distal end of the inner shaft is advanced beyond the stone. Basket 20 may then be advanced out of the inner shaft to allow it to expand, and the whole device may be pulled back to capture the stone. Camera 22 is coaxially located within the retention member shaft (or "basket shaft") and is positioned with its distal end at or near a distal end of the inner shaft and/or the retention member shaft, so that it faces into basket 20 to help visualize the stone and the process of capturing the stone. Once the stone is trapped in basket 20, inflatable balloon 24 may be inflated, typically until it contacts the inner wall of the ureter. Basket 20 and stone may then be pulled back proximally into the distal end of balloon 24, such that balloon 24 invaginates to receive and envelop at least part of basket 20 and stone. At this point, system 10 may be withdrawn from the ureter, with balloon 24 helping to prevent trauma to the ureteral wall and reducing the amount of force required to remove the stone. In some embodiments, irrigation fluid for enhancing visualization and/or lubrication may also be introduced into the ureter during the method. Although suction may also be used in some embodiments to help trap and/or retain the stone in basket 20, it is not a necessary component of the system or method. This is only one embodiment of a method for stone removal, and this embodiment and alternative embodiments are described in further detail below.

In one embodiment, handle extension 14 slides at least partially into and out of handle 12 to advance and retract one or more of the shafts of system 10. Handle extension 14 is an optional feature, and in alternative embodiments it may be eliminated. Additionally, the movements of the various shafts of system 10 described herein are exemplary in nature and should not be interpreted as limiting. Some shafts move relative to other shafts, and some shafts may be fixed relative to handle 12 or handle extension 14. For example, in one embodiment, camera 22 may be fixed to handle 12, so that it does not move during use of system 10, and instead, other parts move around it. This relationship may be advantageous, because it may reduce wear and tear on camera 22, which in some embodiments may be reusable. The inner shaft, which again will be shown and described in greater detail below, may also be fixed to handle 12 in one embodiment, so that the inner shaft covers most or all of the long, thin, flexible portion of camera 22 at all times. In alternative embodiments, however, the various relative movements and relationships described herein may be changed, without significantly changing the overall function of system 10. Therefore, the descriptions of shaft movements, actuators, movement of handle extension 14 and the like should not be interpreted as limiting the scope of the invention as it is described in the claims.

In one embodiment, handle extension 14 is fixedly attached to outer shaft 16, such that handle extension 14 and outer shaft move together, relative to handle 12 and the inner shaft that houses basket 20. Handle extension 14 may slide in and out of handle 12 by manipulating shaft slider 30, which is fixedly attached to extension 14. Handle extension 14 may also include balloon fill port 26, which may be coupled with a source of balloon inflation fluid, such as but not limited to saline solution, water or contrast agent.

Handle extension 14 may also include irrigation port 28, which may be coupled with a source of irrigation fluid, such as but not limited to saline solution, water or a solution including a pharmaceutical agent, such as lidocaine. The irrigation fluid may exit system 10 near the distal (viewing) end of camera 22, for example out of a space between the distal end of the inner shaft and the distal end of the retention member shaft, or alternatively, through one or more irrigation fluid apertures on the inner shaft, the wall retention member or the like. Irrigation fluid may be used, for example, to help enhance visualization by keeping the distal end of the camera 22 clean and/or expanding a collapsed ureteral lumen, thus increasing the ability to visualize the lumen itself. Additionally, irrigation fluid may help to reduce friction while removing the kidney stone, to reduce pain, for example when lidocaine is used as lubricant, and/or for any combination of these or other purposes. In some embodiments, irrigation fluid may be passed out of the distal end aperture(s) or channel(s) at a low flow rate—for example, less than 5 cc/min. This low flow rate might be lower, for example, than flow rates typically used with currently available endoscopes for irrigation.

In one alternative embodiment, irrigation port 28 and balloon fill port 26 may be combined into a common port fluid infusion port. For example, in one embodiment, inflation fluid may also act as irrigation fluid by exiting out of the inflated balloon through one or more small apertures. Alternatively, fluid may enter the combined port and may then be directed into a balloon inflation lumen and an irrigation fluid lumen.

Handle 12 couples with camera proximal portion 34 and also may include retention member slider 32, which is attached to the proximal end of the retention member shaft. Retention member slider 32 may be used to advance and/or retract basket 20 out of and/or into the inner shaft. Handle 12 also provides a portion of system 10 that a user may conveniently grasp with one hand. Slider(s) 30 and/or 32 may be manipulated with the same hand that holds handle 12 or with the opposite hand. Handle 12 and handle extension 14 may be made of metal, polymer, a combination of metal and polymer, or any other suitable material or combination of materials. Outer shaft 16 may be made of any suitable, biocompatible, flexible polymer. In some embodiments, system 10 may be fully disposable. In alternative embodiments, camera 22 may be reusable, and the rest of system 10 may be disposable. Finally, it may be possible that in some embodiments all of system 10 may be reusable and sterilizable, such as by autoclave or other sterilization processes.

In some embodiments, the proximal end of outer shaft 16 may removably attach to the distal end of handle extension 14, for example by a snap-on fit in one embodiment. This snap-on configuration may have two primary advantages. First, outer shaft 16 may be attached to handle 12 after shaft 16 has been advanced into the ureter through an endoscope (such as but not limited to a cystoscope or steerable shaft) to position the distal end of shaft 16 in a desired location for stone removal. This allows the physician user to remove the endoscope after positioning the outer shaft 16 and prior to operation, improving patient comfort and ease of use. Second, handle 12 may be reusable, even if some or all of the rest of system 10 is disposable.

Referring now to FIGS. 2A and 2B, a distal portion of system 10 is illustrated in greater detail. In these figures, a kidney stone S is shown trapped inside basket 20. In some embodiments, balloon 24 (an "everting balloon," as described above) may have several distinct portions, such as a proximal attachment portion 35 attached to outer shaft 16, a proximal tapered portion 36, a middle portion 37, a distal tapered portion 38 and a distal attachment portion 39 attached to a wall protection member shaft 42. Generally, it may be advantageous for distal tapered portion 38 to preferentially collapse into balloon 24 (referred to as "everting" or "invaginating"), when basket 20 and stone S are pulled back into distal tapered portion 38, rather than having proximal tapered portion 36 collapse. This preferential eversion/invagination of distal tapered portion 38 may be referred to in this application as an "eversion bias" of balloon 24—i.e., distal tapered portion 38 everts/invaginates preferentially, while proximal tapered portion 36 retains at least approximately its original configuration and does not collapse.

One way to achieve eversion bias in balloon 24 is to provide proximal tapered portion 36 with a more gradual taper than distal tapered portion 38. For example, in some embodiments, proximal tapered portion 36 may have a taper angle of between about 5 degrees and about 25 degrees, and ideally between about 10 degrees and about 15 degrees, relative to a longitudinal axis of balloon 24. Distal tapered portion 38 may have a taper angle of between about 30 degrees and about 90 degrees, and ideally between about 40 degrees and about 70 degrees, relative to the longitudinal axis of balloon 24. In one specific example, distal tapered portion 38 may have a taper angle of about 45 degrees, and proximal tapered portion 36 may have a taper angle of about 10 degrees. The "steeper" taper angle of distal tapered portion 38 relative to that of proximal tapered portion 36 will cause distal tapered portion 38 to preferentially collapse into balloon 24, when basket 20 and stone S are pulled back into distal tapered portion 38, rather than having proximal tapered portion 36 collapse. Additionally, the steeper taper angle of distal tapered portion 38 may facilitate engulfing the stone with balloon 24 with less relative movement between outer shaft 16 and wall protection member shaft 42. In some embodiments, proximal tapered portion 38 may also collapse, at least slightly, but only after distal tapered portion 38 has collapsed first.

FIG. 2B illustrates this preferential eversion or invagination of distal tapered portion 38. Although distal tapered portion 38 is not visible in FIG. 2B, it has been pulled back into balloon 24 by basket 20 and stone S, while middle portion 37 and proximal tapered portion 36 remain approximately in their original configuration. As basket 20 and stone S are pulled further into balloon 24, part of middle portion 24 may be made to invaginate into the interior of balloon 24, and in this way all or part of stone S may become encircled/surrounded by balloon 24. Basket 20 and stone S may be pulled proximally by sliding the retention member shaft (not visible here, because it is within wall protection member shaft 42 and the inner shaft) proximally, for example via a slider on handle 12 or handle extension 14. Pulling basket 20 and stone S proximally into balloon 24 may cause wall protection member shaft 42 to slide proximally, as balloon 24 invaginates. Balloon 24 may also be invaginated, in some embodiments, by actuating an eversion or wall protection member slider, which may be coupled with the wall protection member shaft 42. In some embodiments, distal attachment portion 39 and proximal attachment portion 35 may be of approximately equal lengths. Alternatively, they may have different lengths.

Balloon 24 may serve a number of different functions. For example, balloon 24 may reduce friction against the ureter wall by the trapped stone during removal, it may reduce trauma of the ureter wall by sharp edges of a trapped stone, and/or it may help retain the stone within system 10 in general. The retaining function may occur if balloon 24 surrounds the stone partially or completely and thus helps with the trapping/retaining of the stone. In other words, balloon 24 and basket 20 may work together to trap and retain the stone.

In some embodiments, as an alternative or in addition to having different taper angles, distal tapered portion 38 and proximal tapered portion 36 may also have different thicknesses, be made of different materials, include one or more rigidity and/or flexibility features, and/or the like. In some embodiments, for example, proximal tapered portion 36 may be thicker than distal tapered portion 38, again to promote preferential collapse/invagination of distal tapered portion 38 before any other portion of balloon 24. In one embodiment, for example, a thicker balloon wall of proximal tapered portion 36 may be achieved in a dipping manufacturing process by dipping proximal tapered portion 36 more times than distal tapered portion 38. In other embodiments, where balloon 24 is formed using a balloon blowing process, an additional layer at proximal tapered portion 36 may be added after formation of balloon 24. This layer may be a simple adhesive, additional balloon material, or some other material that will bond to the blown balloon surface. Additionally or alternatively, the blown balloon 24 may be preferentially stretched to form a thinner distal tapered portion 38. In various embodiments, for example, proximal tapered portion 36 may have a wall thickness that is about 25 percent to 125 percent greater than a wall thickness of distal tapered portion 38.

Another way to facilitate eversion bias in balloon 24 is to have a distal tapered portion 38 with a lower durometer (i.e., softer) than that of proximal tapered portion 36. A higher durometer material is, in general, stiffer and more difficult to evert than a lower durometer version of the same material or a different material with lower durometer. Providing proximal tapered portion 36 with a durometer that is at least about 5 percent greater than the durometer of distal tapered portion 38 may cause distal tapered portion 38 to evert very preferentially relative to proximal tapered portion 36. In some embodiments, the variance may be created by dip forming balloon 24 in two different durometers of material. In other embodiments, proximal tapered portion 36 may be coated in a different material of higher durometer than a material of distal tapered portion 38. In some embodiments, a coating may be used on balloon 24 to create an eversion bias via a combination of increased wall thickness and higher durometer material on proximal tapered portion 36, relative to distal tapered portion 38.

Figure 2C:
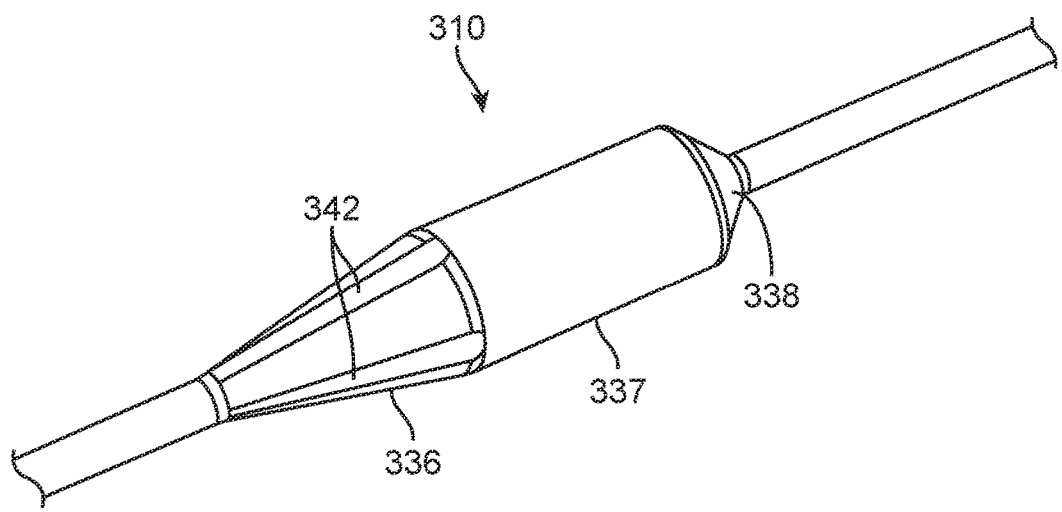
FIGS. 2C and 2D are perspective views, respectively, of an inflatable balloon portion of an obstruction removal device and a mandrel on which the inflatable balloon portion may be manufactured, according to one embodiment.
Figure 2D:
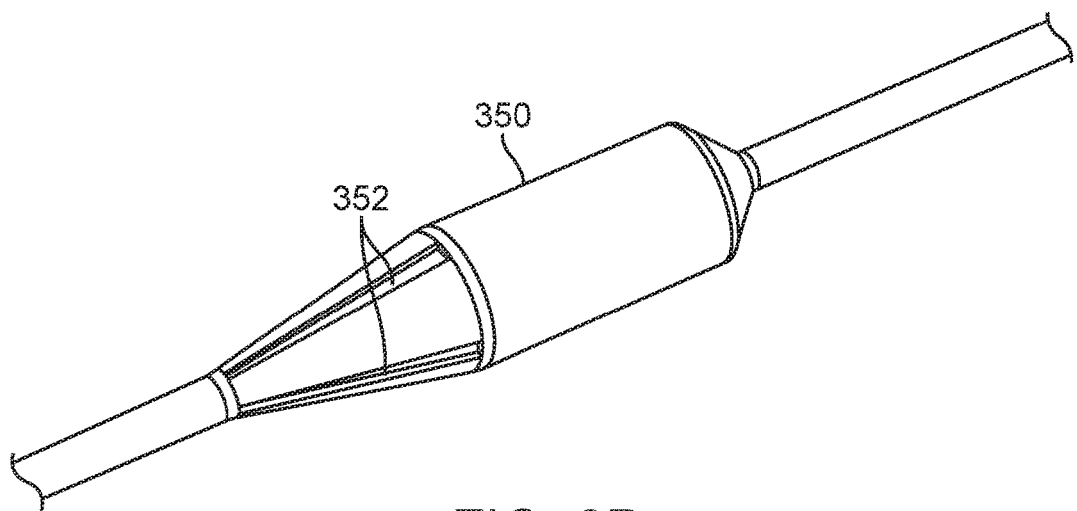

Referring now to FIGS. 2C and 2D, as mentioned above, another way to achieve eversion bias in favor of a distal tapered portion 338 of a balloon 310 is to include multiple rigidity features on a proximal tapered portion 336 of balloon 310. In the embodiment shown in FIG. 2C, the rigidity features are multiple, longitudinally oriented ribs 342. In one embodiment ribs 342 may be formed, for example, during the blowing/dipping balloon formation process, by adding grooves 352 to a mandrel 350 (FIG. 2D) used to form balloon 310. Alternatively, ribs 342 may be added after balloon formation by applying axial lines of adhesive or other material that bond to the outer surface of balloon 310. Examples of such materials may include, but are not limited to, UV cure adhesive and polyurethane, nylon, and polyether block amide dissolved in a solvent solution. Alternatively, ribs 342 made from polymer or metal strips may be bonded to outside of balloon 310. Ribs 342 may be made out of a variety of materials and may provide additional proximal eversion resistance through increased thickness and/or by using a material of increased rigidity, stiffness and/or durometer. Alternatively, ribs 342 may be formed in balloon by laser cutting an outer shaft of the catheter where balloon 310 is bonded to the catheter. As is apparent from FIGS. 2C and 2D, balloon 310 may be provided with different taper angles (distal tapered portion 338 having a steeper angle than proximal tapered portion 336) and ribs 342 or other rigidity features. In fact, any suitable combination of taper angles, rigidity features, thicknesses, materials and/or the like may be used in a given balloon embodiment to achieve a desired level of stiffness, flexibility and eversion bias.

In addition (or as an alternative) to the everting balloon features and manufacturing methods described above for providing eversion bias in favor of a distal tapered portion, in some embodiments eversion bias may be created by using balloon "memory." This may be achieved, for example, by aiding the initial few eversions of balloon 24 during manufacturing, to create eversion creases, folds or thinning in distal tapered portion 38 prior to use. These initial eversions may be performed on balloon 24 at any time after balloon 24 is formed and before its clinical use. The general principle is to use a support or fixture to force distal tapered end 38 to evert. In some embodiments, a support fixture may be made for use with balloon 24, while in other embodiments, a user may use his/her fingers to support or stretch proximal tapered portion 36 to force distal tapered portion 38 to evert first. After an initial eversion, balloon 24 begins to develop eversion bias through the creation of balloon folds and thinning at distal tapered portion 38. In some embodiments, balloon 24 may be heated to above about 50 degrees Celsius to help set the eversion bias more permanently into balloon 24, due to material property changes that occur in balloon 24 at the selected temperature. Such heating memory is sometimes used for balloon folding, to reduce the profile during deployment.

Another factor that contributes to a desired eversion of distal tapered portion 38 of balloon 24 is the outflow of the balloon inflation fluid during eversion. In various embodiments, everting balloon 24 may be inflated with any suitable fluid or gas, such as but not limited to air, water, saline or radiopaque die. The inflation substance in balloon 24 is evacuated out of balloon 24 during eversion, as the interior volume of balloon 24 decreases. If the fluid evacuates too easily, balloon 24 may not hold its shape during eversion, and it may collapse. If it is too difficult for the fluid to evacuate, it may require excessive force or even be impossible to evacuate the fluid. This may also lead to an increase in fluid pressure within balloon 24, which is often undesirable. Maintaining a low balloon inflation pressure (below about 5 atmospheres, and ideally about 2 atmospheres or less) allows balloon 24 to better conform to the surrounding tissue structure and prevents trauma to surrounding tissue during the eversion.

Several critical factors influence balloon evacuation during eversion. One factor is the cross-sectional area of the fluid channel in the catheter. The cross sectional area is the filling area along the catheter length. While this is generally the same along the length, it is also possible to create a choke point or widening for additional control. One way to do this is by under- or over-sizing a thermal bond diameter for the proximal end of balloon 24. As an example, using a smaller thermal bonding jaw diameter than that of the catheter would result in a choke point of reduced cross-sectional area. This could be used to adjust the cross-sectional area during manufacturing, to prevent balloon 24 from evacuating too easily and to better control eversion of balloon 24.

Another factor that influences balloon evacuation is the characteristics of the fluid used to fill balloon 24. For example, a lower viscosity fluid results in lower resistance to evacuation. The balloon inflation pressure is another factor, with lower pressures generally resulting in easier evacuation. Yet another factor is the resistance generated in the inflation fluid dispenser, such as but not limited to a syringe. A smaller syringe, for example, requires more plunger displacement to evacuate the fluid and results in an increased resistance to fluid evacuation. In some embodiments, a liquid such as water or saline may be used as the inflation fluid, which may provide a desirable compromise between viscosity, pressure and the cross-sectional channel availability in catheters between 2 F and 8 F in diameter. Depending on catheter and balloon orientation, it may be acceptable to fill with a mixture of fluid and gas, in particular if the balloon is oriented vertically with the distal end facing up. In some embodiments, having gas bubbles in the distal tip may improve the eversion bias of balloon 24. Properly balancing the various evacuation variables facilitates evacuation without additional user input.

FIG. 2A illustrates the fact that an optional feature of system 10 is one or more irrigation ports, apertures, openings or the like (not visible in the drawing) for providing irrigation fluid 40 at or near the distal end of system 10. Irrigation fluid 40 may serve the purpose, for example, of helping clean the lens of camera 22, clear the field of vision of camera 22, lubricate contact between system 10 and a ureteral wall and thus reduce friction during stone removal, and/or reduce pain in the case where lidocaine or some other anesthetic is infused into the site. In various embodiments, for example, fluid 40 may exit out of a distal end of system 10 via one or more small apertures in balloon 24 (for example laser-drilled holes that allow fluid to slowly weep out of balloon 24), via an irrigation lumen formed as a space between the inner shaft and the retention member shaft, between camera 22 and the inner shaft, or between the inner shaft and wall protection member shaft 42, or any other suitable fluid lumen or aperture(s). It may be advantageous, for example, to provide irrigation fluid close to the distal end of the camera, for clearing the field of view of the camera. This may be achieved, in some embodiments, by passing irrigation fluid through a space between the inner shaft and the retention member shaft.

Typically, only a low pressure of less than 1 atm is used to inflate balloon 24. This low pressure inflation enhances the ability of balloon 24 to invaginate and in some embodiments to be advanced around the obstruction. Lower pressures are also advantageous in preventing ureteral trauma associated with higher pressure and/or balloon diameters.

Once the obstruction is enveloped, it may often be easiest to remove the obstruction with balloon 24 partially or entirely deflated. In one embodiment, using the constant force of a passive syringe, coupled with removal system 10 and balloon 24 (via balloon inflation port 26), it is possible to allow balloon 24 to deflate automatically due to the force placed on balloon 24 when basket 20 and stone S are pulled back into balloon 24. In other words, the force and volume of basket 20 and stone S being pulled into balloon 24 reduces the capacity of balloon 24 to hold fluid volume, which in turn pushes the fluid back up the balloon inflation lumen toward balloon fill port 26 and an attached syringe (or other fluid infusion source). In the case where the infusion source is a syringe, this fluid pressure will be sufficient to push an unobstructed syringe plunger back, allowing balloon 24 to passively deflate. Other configurations employing stop valves and/or pressure monitoring are also possible, in alternative embodiments.

In some embodiments, to aid in detection, it may be beneficial to expand the ureter between the obstruction and the removal device. In particular, if the ureter is collapsed, then expanding it allows for better visualization. In the ureter, for example, about 1-2 cc of fluid can often provide a small amount of passive dilation (about 1-3 mm in a naturally closed orifice), which allows greater obstruction visualization. The dilation fluid used may be water, saline, or a combination of either with an analgesic agent. The fluid may be introduced into the lumen/vessel in a variety of ways. For example, a kidney stone removal device may emit a layer of fluid through relatively low-flow rate nozzles to dilate the ureter ("hydrodilation"). In various embodiments, for example, the flow rates used may be less than 20 cc/min. This fluid buffer/hydrodilation may be used, for example, to prevent body luminal wall trauma during obstruction removal. A number of nozzle profiles and hydrodilation techniques are described in patent application Ser. No. 13/761,001, which was previously incorporated by reference. The infused liquid (or liquids) may include water, saline, lidocaine and/or other suitable liquid(s).

Additional dilation may also be achieved through small perforations in balloon 24, in some embodiments. Perforations on the order of 0.006" or smaller provide adequate dilation without necessarily flooding the lumen with fluid. In the case of the ureter, this implies minimizing renal pressure. Additionally, small perforations combined with a compliant balloon material allow for the perforations to effectively "seal" under lower pressures, allowing balloon 24 to inflate to a relatively low pressure without liquid leakage. As the pressure is increased, the balloon diameter and fluid pressure increase, allowing liquid to pass through the perforations and into the surrounding ureter or other vessel. This configuration may be advantageous for several reasons. First, it may help prevent over-inflation of balloon 24, by acting as a pressure release mechanism. Second, the released fluid may act as a lubricant, which will further facilitate stone removal. Third, the apertures may facilitate invagination of balloon 24.

A similar perforated design could be used in a non-compliant surface with smaller perforations. In this case, the increased water pressure alone would force the liquid from the non-compliant structure. In such embodiments, portions of the device on which it may be advantageous to add perforations include the instrument shaft, grasper shaft, or inner lumen side-wall, among others.

In various alternative embodiments, a smaller amount and/or flow rate of fluid may be introduced, for example to enhance visualization. This type of fluid introduction/irrigation may provide some amount of passive or slight dilation of the ureter but is not typically designed to provide hydrodilation.

Figure 3A:
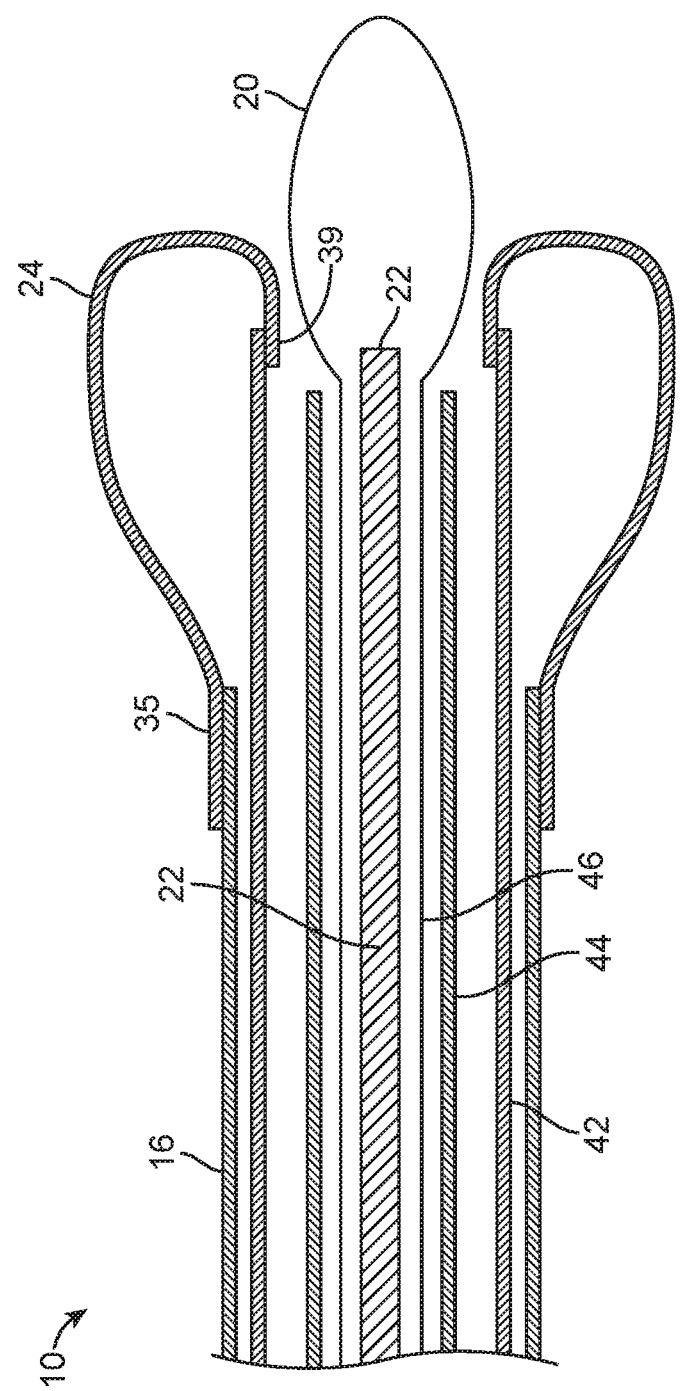
FIGS. 3A and 3B are side cross-section and end-on cross-section views, respectively, of a kidney stone removal system similar to the system of FIGS. 1A, 1B, 2A and 2B.
Figure 3B:
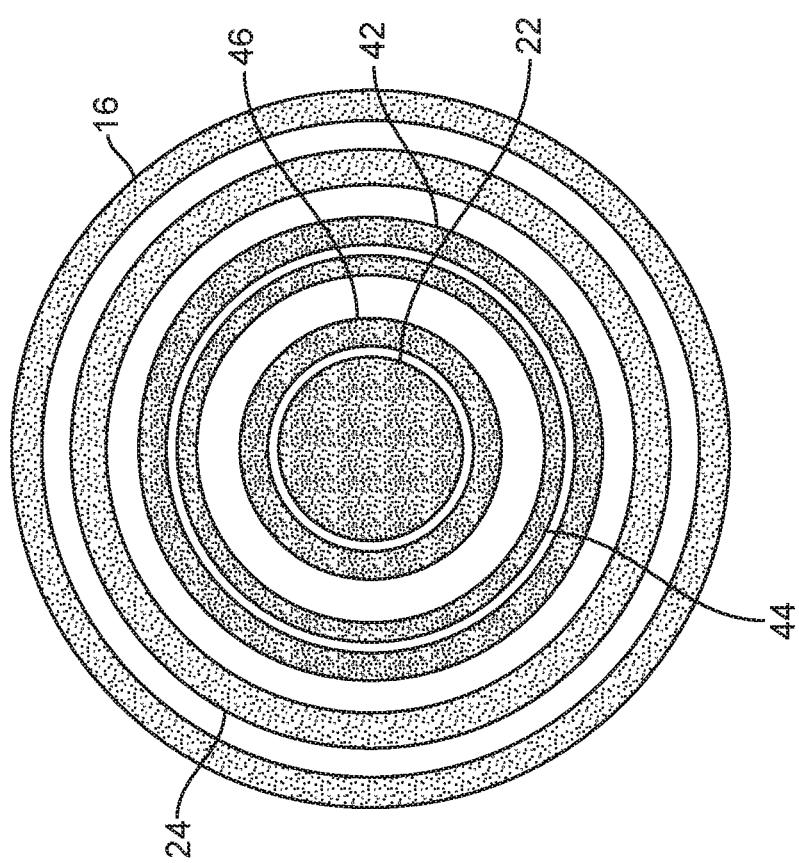

With reference now to FIGS. 3A and 3B, one embodiment of system 10 is illustrated in side cross section and end-on cross section, respectively. Number labels for the components of system 10 are carried over to FIGS. 3A and 3B from those prior figures. Furthermore, neither FIGS. 3A and 3B nor any prior or subsequent figures are necessarily drawn to scale. Referring again to FIGS. 3A and 3B, and moving from outside to inside, system 10 first includes outer shaft 16, which is attached at its distal end to proximal attachment portion 35 of balloon 24, and wall protection member shaft 42 (or "balloon shaft"), which is attached at its distal end to distal attachment portion 39 of balloon 24. Moving inward, the next component is an inner shaft 44, which has been referred to above but is not visible on previous figures. The next shaft moving inward is a retention member shaft 46, which extends distally into basket 20. As discussed above, retention member shaft 46 and basket 20 (or "stone retention portion") may be referred to herein generally as a "stone retention member." In some embodiments, such as the one illustrated in FIGS. 3A and 3B, the stone retention member is one piece, with retention member shaft 46 extending from a proximal end of system 10 to basket 20 at its distal end. In other embodiments, a separate retention member shaft piece may be attached to a separate stone retention portion piece to form the stone retention member.

Camera 22 is housed coaxially within retention member shaft 46, so that its distal end faces into basket 20. In at least one embodiment, camera 22 and inner shaft 44 are both fixed to handle 12, such that the distal end of camera 22 is positioned at or near the distal end of inner shaft. Retention member shaft 46, in this embodiment, is free to slide proximally and distally over camera 22 and within inner shaft 44. This allows basket 20 to be advanced out of, and pulled back into, inner shaft 44, while keeping camera 22 in a fixed position, thus reducing wear and tear on camera 22.

Some of the components of system 10 are movable, relative to other components. One embodiment is described here, but this is only one of a number of potential embodiments. In alternative embodiments, movement of components may be entirely or partially changed, without departing from the scope of the invention. In one embodiment, outer shaft 16 may be fixed to handle extension 14 and thus may slide back and forth relative to handle 12 as handle extension 14 slides back and forth. Wall protection member shaft 42 may be attached to a slider on handle 12 or handle extension 14. In some embodiments, wall protection member shaft 42 may tightly contact the inner wall of outer shaft 16 and may simply move in conjunction with outer shaft 16 via friction force and/or may slide proximally when the stone and basket 20 are pulled into balloon 24. As mentioned above, inner shaft 44 may be fixedly coupled with handle 12, so that it does not move relative to handle 12. Finally, retention member shaft 46 (or "basket shaft") may be coupled proximally with slider 32 on handle 12, so that retention member shaft 46 may be advanced to advance basket 20 out of inner shaft 44. Inner shaft 44, in turn, may be exposed out of the distal end of outer shaft 16 by pulling back on handle extension 14 to pull outer shaft 16 proximally relative to inner shaft 44. In one embodiment, system 10 may be advanced through the ureter with inner shaft 44 extended out of the distal end of outer shaft 16. Alternatively, outer shaft 16 may be retracted later in the process, for example when system is already advanced to a treatment location, to expose inner shaft 44. Either way, the entire system 10 may then be advanced, once inner shaft 44 is extended out of outer shaft 16, to pass the distal end of inner shaft 44 around and past the stone. Basket shaft 46 may then be advanced to expose basket out of the distal end of inner shaft 44. The whole system 10 may then be retracted to trap the stone in basket 20. Camera 22, meanwhile, may be fixedly, though removably, coupled with handle 12, so that it remains in a fixed position relative to the moving components during the process. These and other steps of one method embodiment will be described in further detail below.

A mentioned previously, wall protection member shaft 42 may be mobile relative to outer shaft 16. For example, it may be possible to retract wall protection member shaft 42 as basket 20 and stone are pulled back into balloon 24. Alternatively or additionally, wall protection member shaft 42 may passively move back as basket 20 and stone are pulled into balloon 24. Moving at least some of the components of system 10 relative to other components allows kidney stone removal (or other obstruction removal from other body lumens) using the method briefly described above and described in more detail below. The various components may be made of any suitable materials, such as flexible polymers.

As mentioned above, this combination of moving parts of system 10 may be altered in alternative embodiments. For example, it may be possible in one embodiment to fix outer shaft 16 to handle 12 and have inner shaft 44 slide in and out of outer shaft 16. This is just one potential change that might be made, and the embodiment described here is simply to provide an example.

Figure 4A:
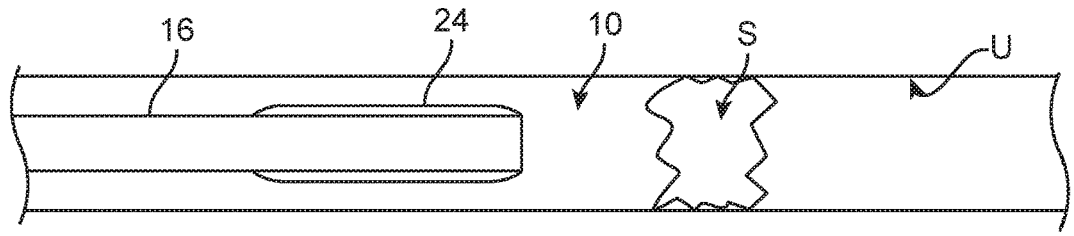
FIGS. 4A-4E are schematic side views of a ureter and kidney stone, illustrating a method for removing a stone from a ureter using a system such as that described in FIGS. 1A, 1B, 2A, 2B, 3A and 3B, according to one embodiment.
Figure 4B:
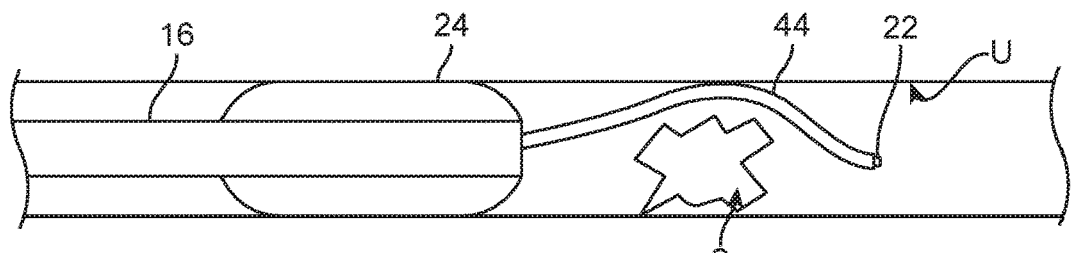

FIGS. 4A-4E illustrate one embodiment of a method for using system 10 to remove a kidney stone from a ureter (or other obstructions from other lumens, in alternative embodiments). FIGS. 4A-4E are not drawn to scale. First, as illustrated in FIG. 4A, the distal end of the kidney stone removal system 10, here shown as outer shaft 16 and balloon 24, is advanced into a ureter U to a position near a kidney stone S, just below the obstruction. Shaft 16 and balloon 24 may be advanced through any suitable endoscope device, steerable shaft, catheter or other introducer device, such as but not limited to a cystoscope (not shown). In some embodiments, camera 22 may be used to visualize/detect the kidney stone S and monitor advancement of system 10 to a desired location in the ureter U relative to the stone S. Next, as illustrated in FIG. 4B, balloon 24 may be inflated, which may help maintain a position of shaft 16 in the ureter U. Then, inner shaft 44, containing basket 20, retention member shaft 46 and camera 22, is advanced past the stone S. Camera 22 may be used to visualize this advancement as well.

Figure 4C:
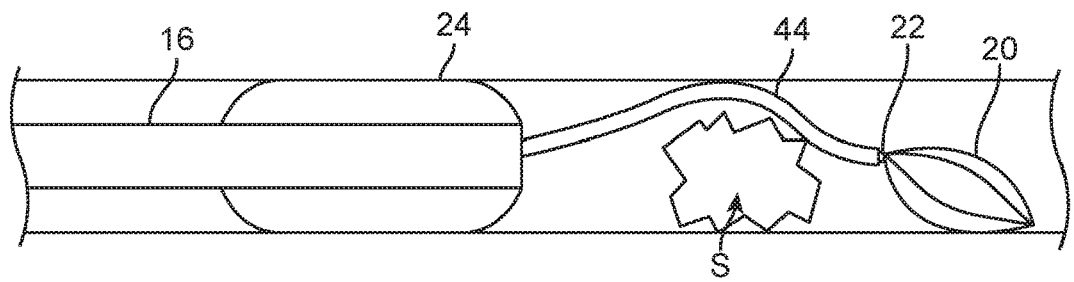
Figure 4D:
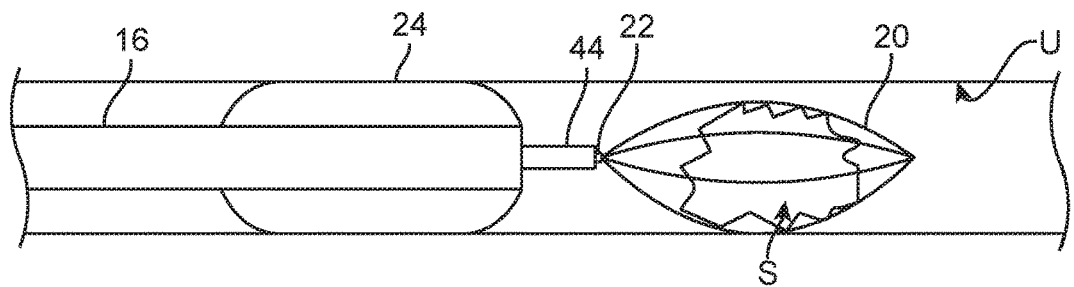
Figure 4E:
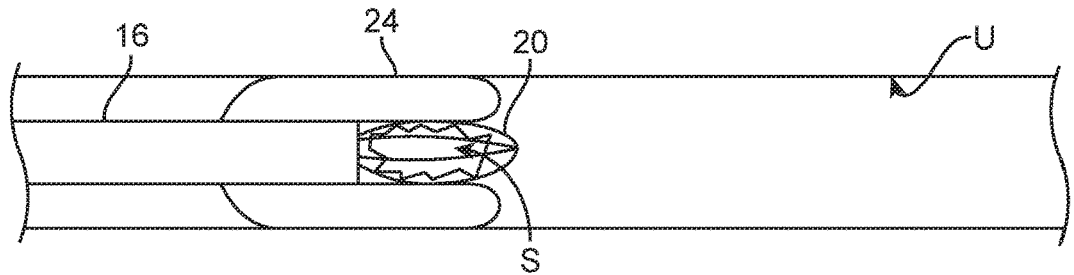

As shown in FIG. 4C, basket 20 may next be advanced out of inner shaft 44, allowing basket 20 to expand. Again, camera 22 may be used to visualize advancement and expansion of basket 20. Next, as illustrated in FIG. 4D, basket 20 may be drawn back proximally (retracted toward outer shaft 16) to capture the stone S by retracting the entire system 10. This step may also be visualized using camera 22. Finally, as illustrated in FIG. 4E, the stone S and basket 20 may be pulled back into balloon 24, by pulling retention member shaft 46 proximally, thus causing balloon 24 to invaginate and at least partially surround the stone S. Balloon 24 will help prevent damage to the wall of the ureter as the stone S is removed, by enveloping the sharp edges of the stone S and thus providing a low-friction surface. The stone S may then be removed by pulling shaft 16 and balloon 24 out of the ureter. Due to the location of camera 22 at or near the distal end of inner shaft 44, any or all of these steps may be visualized via camera 22.

One optional step may involve dilating one or more areas of the ureter by inflating balloon 24 at any point during the stone capture and/or stone removal process. This may be useful, for example, if the system 10 is being removed from the ureter and a constricted or narrowed area is encountered. In one embodiment, balloon 24 may be inflated to dilate at such an area, and then the inflation device, such as a syringe, may be used to actively deflate balloon 24 partially, or alternatively it may simply be allowed to automatically retract to deflate balloon 24 to a nominal pressure for continued removal of system 10 from the ureter.

In some embodiments, handle 12 may include a coupler for coupling camera 22 with inner shaft 44, so that camera 22 is always located at the tip of the inner shaft 44. This ensures full visualization, while preventing having camera 22 protrude beyond the distal end and thus risk being damaged. Some embodiments may also include a frictional fit of basket 20 in inner shaft 44, such that basket motion will be coupled to camera 22 and shaft 44 when not actively controlled by the user, thus eliminating the need to move two sliders at once, while de-coupling the two when active, independent basket control is required. Other unique features of handle 12 are the dual-slider configuration and overall handle shape, which allow single-handed actuation. Yet another feature is the balloon inversion/invagination that is caused by sliding retention member slider 32 until the captured stone is pulled against the tip of wall protection member shaft 42. Further motion of basket slider 32 causes wall protection member shaft 42 to slide proximally relative to the stationary outer shaft 16, which in turn causes balloon 24 to invaginate/invert. This design eliminates the need for an additional "invagination slider." In some embodiments, however, wall protection member shaft 42 will, in fact, be attached to a slider. In some embodiments, this slider may be used to return balloon 24 to its original pre-invagination shape. Such a slide may also be used, of course, to invaginate balloon 24 if necessary.

Figure 5A:
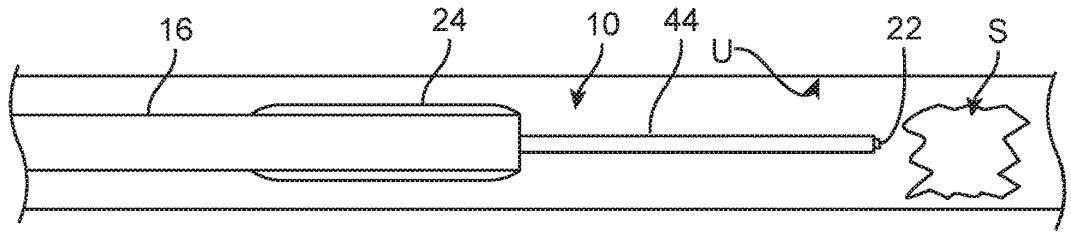
FIGS. 5A-5F are schematic side views of a ureter and kidney stone, illustrating a method for removing a stone from a ureter using a system such as that described in FIGS. 1A, 1B, 2A, 2B, 3A and 3B, according to an alternative embodiment.
Figure 5B:
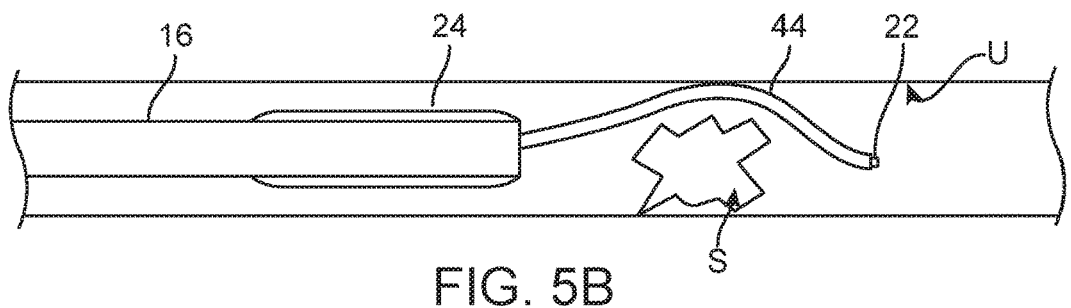
Figure 5C:
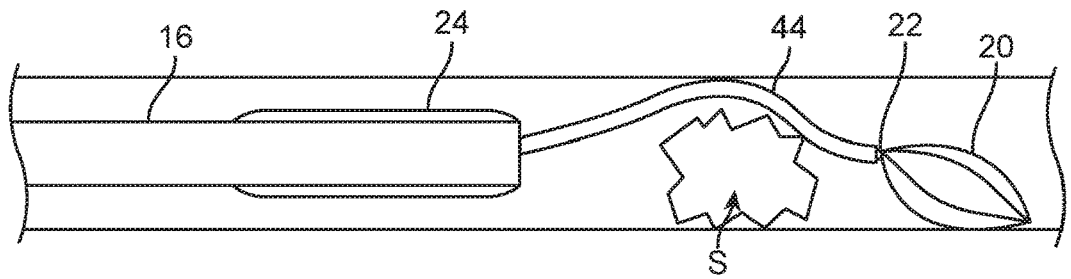
Figure 5D:
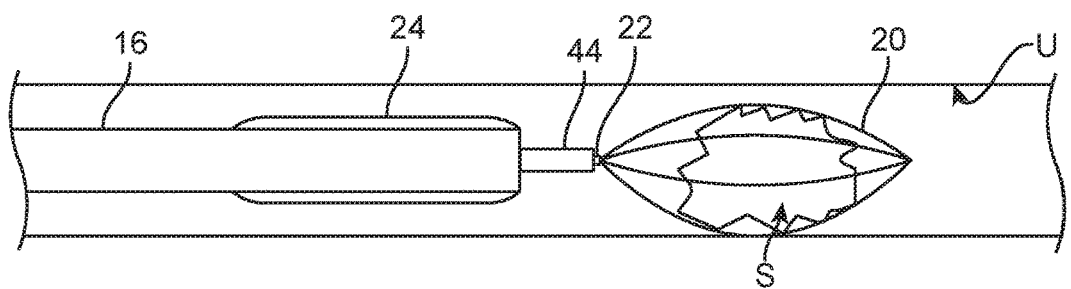
Figure 5E:
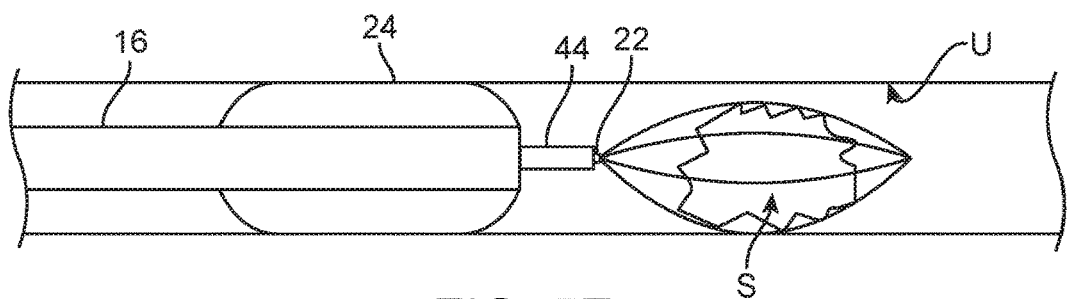
Figure 5F:
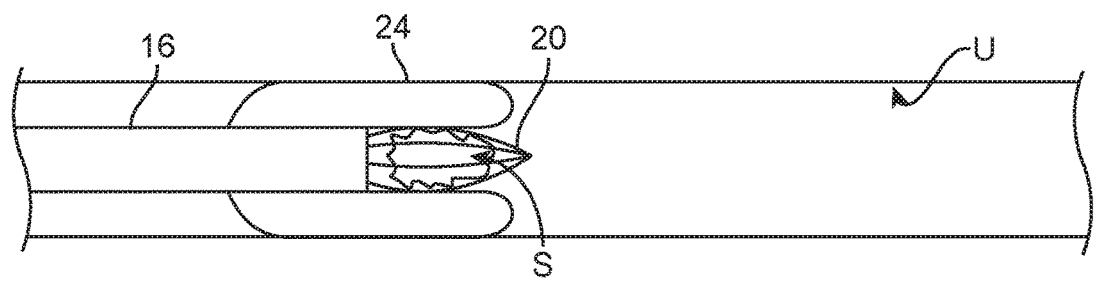

With reference now to FIGS. 5A-5F, another embodiment of a method for removing a kidney stone using system 10 is illustrated. In this embodiment, as illustrated in FIG. 5A, the distal end of the kidney stone removal system 10 is advanced through a ureter U with inner shaft 44 already extended out of the distal end of outer shaft 16 and with balloon 24 deflated. As illustrated in FIG. 5B, all of system 10 may then be advanced further, to position a distal end of inner shaft 44 past the stone S. Still, balloon 24 is in a deflated configuration. As shown in FIG. 5C, basket 20 may next be advanced out of inner shaft 44, allowing basket 20 to expand. Next, as illustrated in FIG. 5D, basket 20 may be drawn back proximally (retracted toward outer shaft 16), by retracting the entire system 10, to capture the stone S. At this point, as illustrated in FIG. 5E, balloon 24 may be inflated. Finally, as shown in FIG. 5F, basket 24 and stone S may be pulled back into balloon 24.

In some cases, this embodiment of the method may be simpler and/or easier to perform than the embodiment described previously. As should be evident from these embodiment descriptions, however, any given method embodiment may include any suitable number of steps and order of steps. Some steps may be eliminated and/or added in various alternative embodiments, without departing from the scope of the invention.

With reference now to FIGS. 6A and 6B, in an alternative embodiment, a kidney stone removal system 110 may include an end effector 118 that has a compliant funnel 124 (or "obstruction shaft"), rather than a balloon, to provide protection for the ureteral wall. End effector 118 may also include an expandable basket 120, a camera 122 and one or more irrigation ports for providing irrigation fluid 140. System 110 may include an outer shaft 116 and some or all of the other components described above in relation to other embodiments. Due to the substitution of funnel 124 for a balloon, however, the design of system 110 may be somewhat simpler. For example, system would not include a wall protection member shaft or a balloon inflation port. Funnel 124 acts in the place of the balloon as a guard against ureter wall trauma during stone removal. As such, funnel 124 may be made of any suitable polymer or other material that helps reduce or minimize friction and/or that can serve as a protective layer to reduce trauma from sharp edges of kidney stones. As illustrated in FIG. 6B, basket 120 and stone S may be drawn back proximally into funnel 124, just as in the embodiment with the balloon, except that funnel 124 does not invaginate or invert. Camera 122 may be positioned at or near the distal end of funnel 124, for visualizing the removal procedure. In alternative embodiments, funnel 124 may be replaced with any other suitable protective, friction/trauma reducing device, such as a shaft, cup, sock, lubricated surface or the like. Optionally, system 110 may include additional ports or apertures, for example at or near the juncture of funnel 124 and shaft 116, for providing lubricating fluid to further facilitate stone removal.

Expandable basket 120 may have a shape that facilitates the expansion of compliant funnel 124 around the stone S and basket 120. As illustrated in FIG. 6A, in some embodiments, expandable basket 120 may have a tapered shape from the portion that retains the stone S toward the connection of basket 120 with the basket shaft (not shown). The tapered shape may help align and expand compliant funnel 124 around the kidney stone S or other obstruction. The expansion of basket 120 may also be used to expand compliant funnel 124 around the obstruction. Using basket 120 to expand complaint funnel 124 makes funnel 124 a passive component, reducing overall complexity of system 110.

Prior to use, complaint funnel 124 often needs to be retained in such a way that it does not catch or rub on either the working channel of the introducing device (cystoscope or other endoscope, for example) or the wall of the body lumen during advancement. One solution would be to provide system 110 with an outer shaft that can slide over funnel 124 to prevent it from expanding prior to capturing the obstruction. Due to space constraints, however, it may be advantageous to eliminate an external shaft from the device assembly. One such solution is to invert funnel 124 inside outer shaft 116 around basket 120 during advancement to the obstruction. When basket 120 is advanced out of the main assembly, funnel 124 is deployed into position (as in FIG. 6A). A variety of variations to this deployment method using other aspects of catheter assembly (camera lumen or fluid introduction lumen, for example) may be possible and will all function in an essentially equivalent manner to the above embodiment.

The embodiments thus far have involved systems in which expandable baskets are used to trap a stone and pull it back into a protective element, such as a balloon or compliant funnel. A different group of embodiments eliminates the expandable basket and instead traps the stone or other obstruction from the side of approach of the device toward the stone. For example, these embodiments typically involve expandable graspers or expandable funnels that are advanced directly over/around the stone and thus used to pull the stone out of the ureter. Some of these embodiments may also involve the use of suction to help pull the stone into the grasper. Several examples of such embodiments are described further below.

Figure 7A:
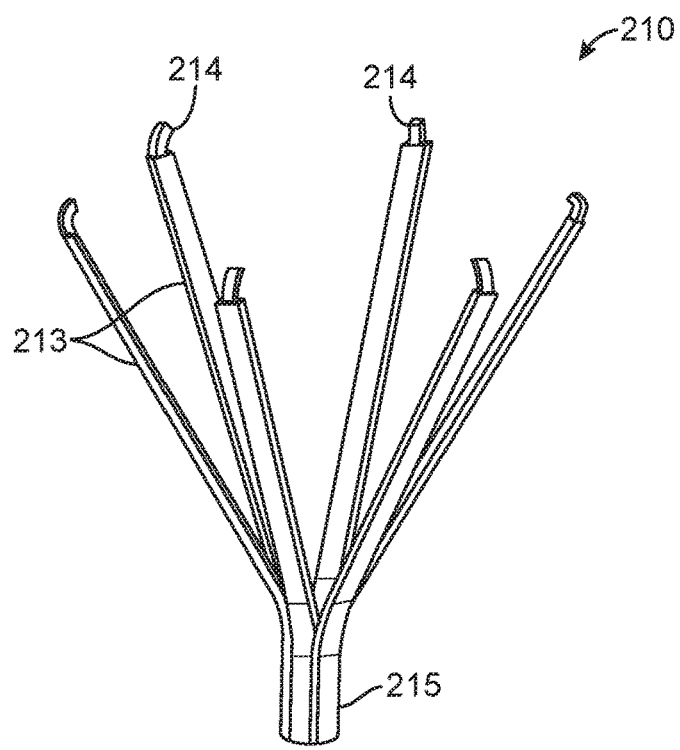
FIGS. 7A and 7B are perspective and close-up views, respectively, of an expandable grasper that may be a part of a kidney stone removal system, according to an alternative embodiment.
Figure 7B:
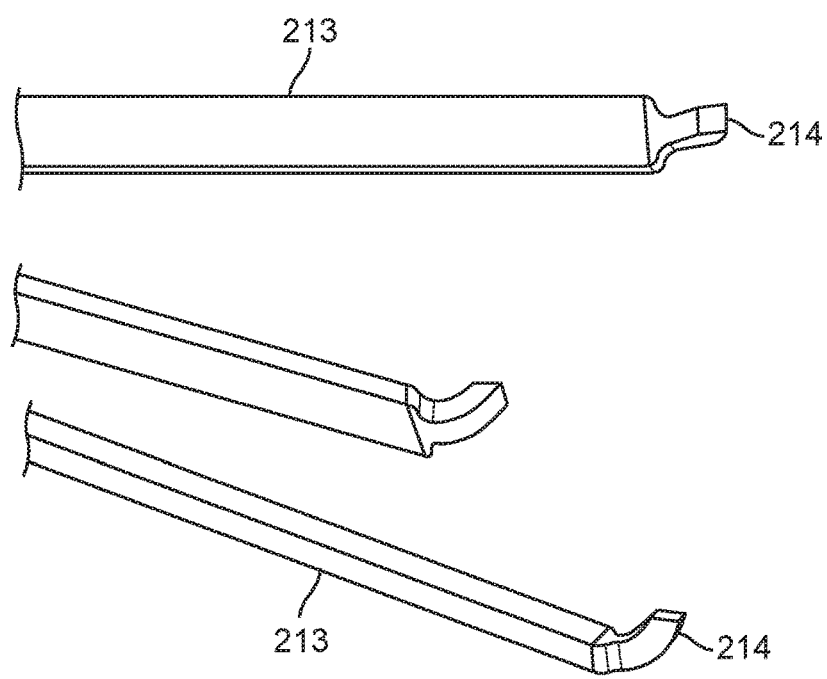

With reference now to FIGS. 7A and 7B, one example of an expandable grasper 210 that may be used to retain a stone or obstruction may include multiple struts 213, each having a hooked distal tip 214. As illustrated in FIG. 7A, the struts 213 are typically joined together at a proximal end 215. (FIG. 7B is a close-up view of several struts 213 and distal tips 214.) Expanding grasper 210 may include any suitable number of struts 213, and struts 213 may include any of a number of differently shaped distal tips 214, according to various alternative embodiments. In some embodiments, distal tips 214 of struts 213 of expandable grasper 210 may be folded inward to form hooks or "teeth," to help retain the kidney stone within grasper 210. Typically, although not necessarily, grasper 210 will be combined with some form of protective coating, membrane, balloon or other protective component to reduce or minimize trauma to the ureteral wall during stone removal. When grasper 210 is advanced out of a shaft in which it is housed, it will expand to a diameter sufficient to grasp a kidney stone. When grasper 210 is then at least partially retracted (drawn back) into the shaft, grasper 210 will contract at least slightly to grasp and hold the kidney stone.

In some embodiments, expanding grasper 210 may be configured to expand automatically when released from a shaft. In such embodiments, for example, expanding grasper 210 may be made by shape setting Nitinol or pre-bending an elastic material such as spring steel or PEEK into the desired expanded geometry. The geometry can then be elastically compressed into a much smaller (unexpanded) shape within the shaft (for example, catheter shaft having a diameter of 6 French or smaller). Expanding grasper 210 may be deployed by advancing grasper 210 out of the shaft and/or sliding the shaft back from the grasper 210. Both result in less constraint on the grasper 210, causing struts 213 to spread apart at their distal ends, thus increasing the diameter of the distal end of grasper 210.

Figure 8A:
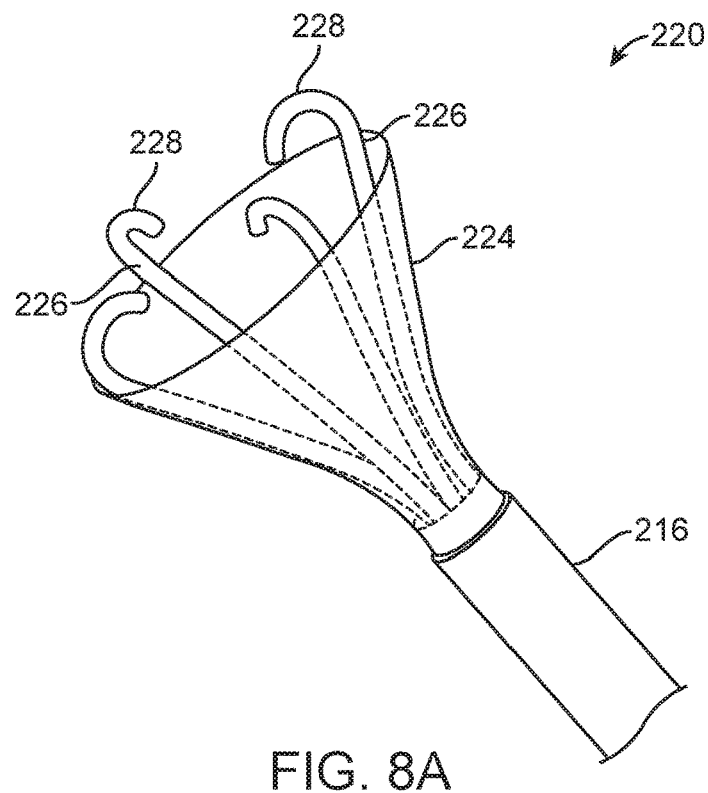
FIGS. 8A and 8B are perspective views of a distal portion of a kidney stone removal system (FIG. 7B shown within a ureter with a kidney stone) having an expandable grasper and a compliant membrane, according to an alternative embodiment.
Figure 8B:
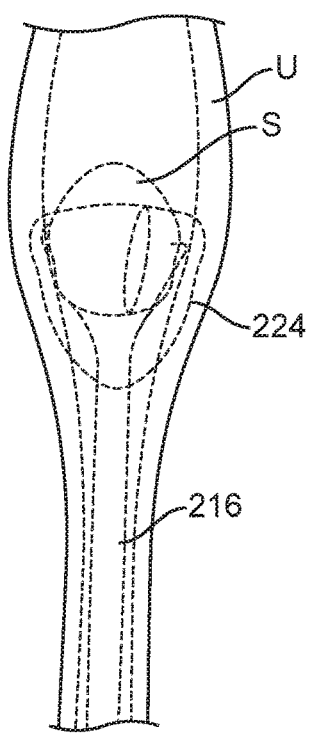

Referring to FIGS. 8A and 8B, another alternative embodiment of a stone removal device 220 may include an outer shaft 216, an expandable grasper 226, with multiple struts and curved distal tips 228, and a protective membrane 224 positioned around grasper 226. FIG. 8B shows device 220 in place within a ureter U and partially surrounding a kidney stone S. In various embodiments, membrane 224 may be made of any suitable polymer or other flexible material and may be configured to prevent trauma to an inner wall of the ureter U once the kidney stone S is captured therein. In various embodiments, membrane 224 may be one layer of material, multiple layers of material, an inflatable balloon, a funnel, a cup, a sock or the like. In some embodiments, grasper 226 and membrane 224 may be housed within outer shaft 216 during advancement of device 220 through the ureter, and then advanced out of the end of outer shaft 216 to expand and then trap a kidney stone S. In some embodiments, and with reference to FIG. 7B, grasper 226 and membrane 224 may expand until they match or slightly exceed the horizontal diameter of the kidney stone S to be removed. In some embodiments, grasper 226 may be advanced out of outer shaft 216 by an amount that achieves a desired diameter.

FIG. 8B illustrates part of a method for removing a kidney stone S from a ureter U, using removal system 220. As illustrated here, system 220 is advanced to a location in the ureter U adjacent the stone S. Expandable grasper 226 is then advanced out of outer shaft 216 (and/or outer shaft 216 may be retracted back from grasper 226), to allow grasper 226 to expand to its expanded, default configuration, such that distal tips 228 are configured in a diameter as wide or wider than the stone S. Grasper 226 may then be advanced over the stone S, thus capturing the stone S in grasper 226. Protective membrane 224 acts to protect the inner wall of the ureter U while removal system 220 is used to pull the stone S out of the ureter U.

In some embodiments, a kidney stone removal system may include, or may be used in a system including, a mechanism for dilating the ureter. For example, in one embodiment, a stone removal system may include a balloon that encases grasper 210 or 226. The balloon may be infused with air, water, saline, a biocompatible lubricant, a local anesthetic (such as lidocaine), any other suitable substance, or a combination of any of these substances, to achieve a desired viscosity, cost, and/or performance. The balloon may provide a smooth surface around the obstruction, reducing removal friction and facilitating passage. In addition, the balloon can be integrated in such a way that inflation causes an additional retention force on the obstruction by inflating the side of the balloon on the inside of struts around the stone.

In alternative embodiments, dilation of the ureter (or other body lumen in other embodiments) may be performed via hydrodilation, without the use of a balloon. Numerous embodiments of devices and methods for hydrodilation of body lumens, such as the ureters, are described in pending U.S. patent application Ser. No. 13/716,001 (Pub No. 2013/0165944), entitled "Apparatus, Systems, and Methods for Removing Obstructions in the Urinary Tract," the full disclosure of which is hereby incorporated by reference herein. Many of the embodiments described in the above-reference patent application use jets to propel fluid against the wall of the ureter to provide hydrodilation. These embodiments may be combined with the embodiments described herein, such that the hydrodilation jets may be used to dilate up and around a kidney stone from the proximal end (or "base") of an expandable grasper, for example. Alternatively, in one embodiment, hydrodilation may be achieved by ejecting fluid out of hollow tines of an expandable grasper (not illustrated)—i.e., using hollow grasping members as water channels with holes near the tips for water ejection.

Figure 9:
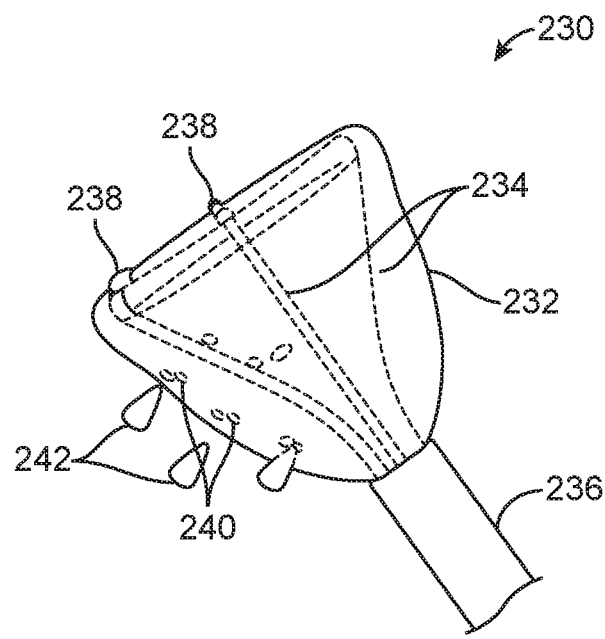
FIG. 9 is a side view of a distal portion of a kidney stone removal system having an expandable grasper and an inflatable balloon, according to an alternative embodiment.

Referring to FIG. 9, in another alternative embodiment, a kidney stone removal device 230 may include an expandable grasper having multiple struts 234 with hooked distal tips 238, a dilation balloon 232 coupled with struts 234, and a shaft 236 for containing the grasper and balloon 234 during delivery into the ureter. Dilation balloon 232 may include multiple apertures 240 (or "holes" or "perforations") to allow fluid 242 to pass from balloon 232 into the region around the obstruction. For example, a local anesthetic may be used to numb the region around the obstruction, a lubricant may be desired for further reduction of friction around the stone, and/or any of the fluids mentioned above may be used to provide hydrodilation force around balloon 232 to reduce friction and/or tissue trauma.

In the embodiment illustrated in FIG. 9, balloon 232 is positioned on removal device 230 on the outside of struts 234. Balloon 232 may be infused with air, water, saline, a biocompatible lubricant, a local anesthetic (such as lidocaine), any other suitable substance and/or a combination of substances. Attaching balloon 232 to the outside surface of struts 234 allows struts 234 to have hooks 238 (or teeth, etc.) to increase the retention force on the stone, without risk of balloon perforation.

Figure 10:
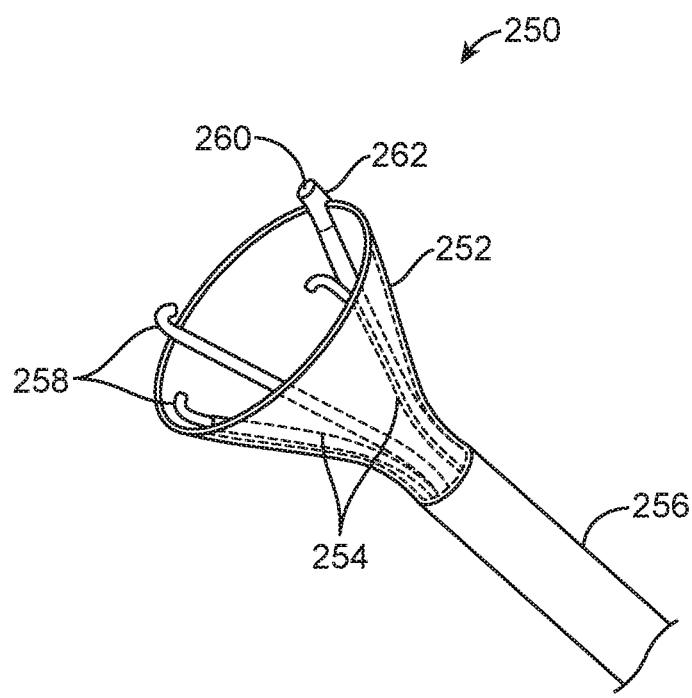
FIG. 10 is a perspective view of a distal portion of a kidney stone removal system having an expandable grasper, a compliant membrane and a camera, according to an alternative embodiment.

Referring now to FIG. 10, as mentioned above, any of the embodiments of obstruction removal devices described herein may include, or may be used with a system that includes, one or more obstruction detection components. These obstruction detection components may be specifically configured for kidney stone detection in some embodiments. FIG. 10 illustrates another embodiment of a kidney stone removal device 250, including an expandable grasper having multiple struts 254 with hooked distal tips 258, a compliant membrane 252 coupled with struts 254, one hollow strut 262, a small camera 260 extending through the lumen of hollow strut 262, and a shaft 256, which the other components are advanced out of and refracted back into. In one embodiment, for example, hollow strut 262 may have a lumen with an inner diameter of about 0.4 mm. This lumen is large enough for a small fiber camera 260 to visualize a kidney stone directly. Illumination for small fiber camera 260 may be provided, in some embodiments, around the sides of camera 260. Alternatively, illumination may be provided via a light source, such as a fiber, directed through a central lumen of shaft 256. In various alternative embodiments, fiber camera 260 may be either reusable or disposable. In other alternative embodiments, an inductance coil or impedance sensor may be included for detection purposes, for example for use in smaller lumens.

Figure 11A:
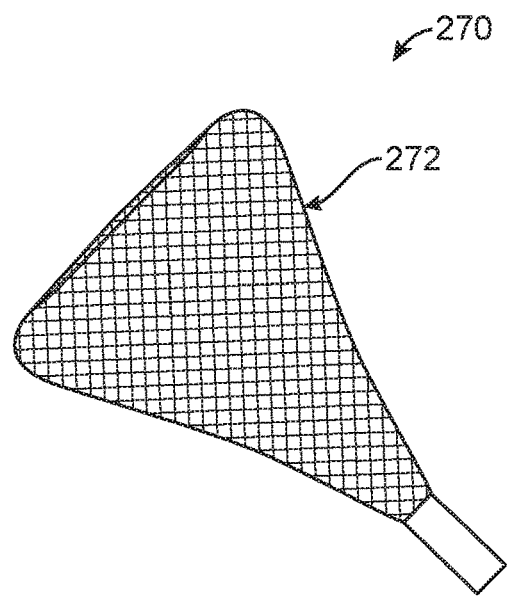
FIGS. 11A and 11B are side views of a distal portion of a kidney stone removal system having an expandable mesh basket and an inflatable balloon, according to an alternative embodiment.
Figure 11B:
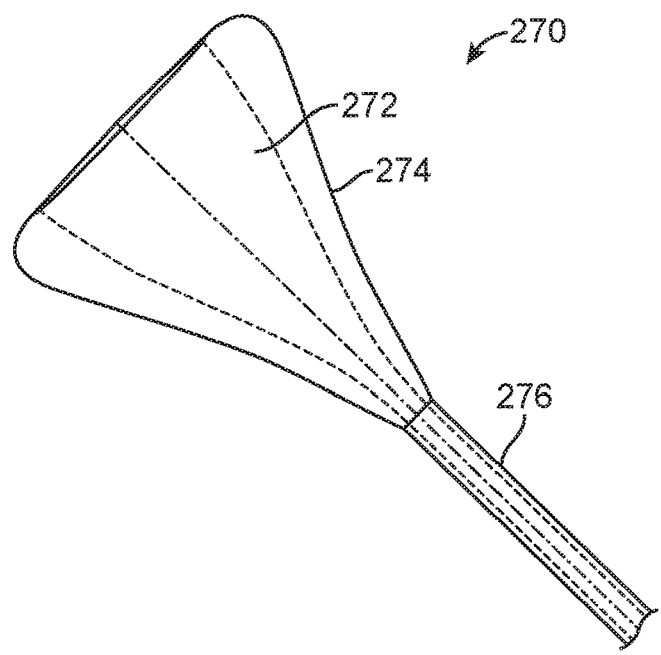

Referring now to FIGS. 11A and 11B, in another embodiment, a kidney stone removal device 270 may include an expandable mesh grasper 272, positioned inside an inflatable balloon 274 (or alternatively a membrane or other friction reducing/protective member), and a shaft 276 for housing both. In one embodiment, expandable mesh grasper 272 may be made of a shape-memory material and may have a configuration similar to that of a vascular stent. Grasper 272 may be constructed from a number of highly compliant materials, such as Nitinol, spring stainless steel, or PEEK plastic, among others. The geometry can then be elastically compressed into a much smaller (unexpanded) shape within shaft 276 (for example, a 6 French catheter shaft). Grasper 272 may then be deployed by advancing grasper 272 out of shaft 276 and/or sliding shaft 276 back from the grasper 272. Either of these methods results in reduced constraint on the expandable member 272, causing the tip diameter to increase. This diameter can then be expanded until it matches the horizontal diameter of the stone. In some embodiments, the tips of expandable grasper 272 may be turned/folded inward to form "teeth" to help retain the stone, similar to the hooks/teeth described above. As mentioned above, in various alternative embodiments, expandable grasper 272 may be combined with any other suitable protective member in place of balloon 274.

Referring to FIG. 11B, in some embodiments, balloon 274 may be infused with air, water, saline, a biocompatible lubricant, or a local anesthetic (such as lidocaine). A combination of any of the above may also be used to achieve a desired viscosity, cost, clinical performance, functional performance, and/or the like. Balloon 274 creates a smooth surface around the obstruction, reducing removal friction and facilitating passage. In addition, balloon 274 may be integrated in such a way that inflation causes an additional retention force on the stone buy inflating the side of balloon 274 on the inside of mesh grasper 272 around the stone. As described above in relation to other embodiments, balloon 274 may also include apertures or perforations to allow fluid to pass from balloon 274 into the region around the obstruction. For example, a local anesthetic may be used to numb the region around the obstruction, a lubricant may be desired to reduce the friction of the obstruction on the surrounding wall, or any of a number of fluids may be used to provide a hydrodilation force around balloon 274 to reduce friction and/or tissue trauma.

As illustrated in FIG. 11B, in some embodiments, balloon 274 may be positioned on the outside surface of mesh grasper 272. Having the balloon attached solely to the outside surface of balloon 274 allows grasper 272 to have "teeth" to increase the retention force on the stone without risk of balloon perforation.

Figure 12:
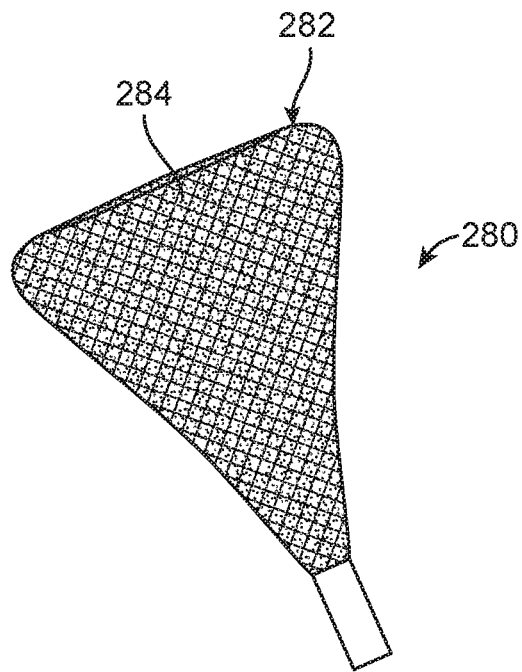
FIG. 12 is a perspective view of a distal portion of a kidney stone removal system having an expandable mesh basket and a webbing between the mesh, according to an alternative embodiment.

Referring now to FIG. 12, in another alternative embodiment, a stone removal device may include an expandable mesh grasper 280 that includes a mesh 282 and webbing 284 disposed between or over mesh 282. Webbing 284 may comprise a highly complaint material, which may be applied to mesh 282 via a dipping process, for example, thus forming a smooth surface for the natural dilation created by grasper 280, and thus reducing the friction required for obstruction removal. In one embodiment, a hydrodilation fluid may be emitted from a portion of webbing 284. Alternatively, hydrodilation fluid may be provided using any of the methods described above. In one embodiment, webbing 284 may serve as the protective element, eliminating the need for an additional element, such as a balloon, funnel-shaped membrane or the like.

Figure 13A:
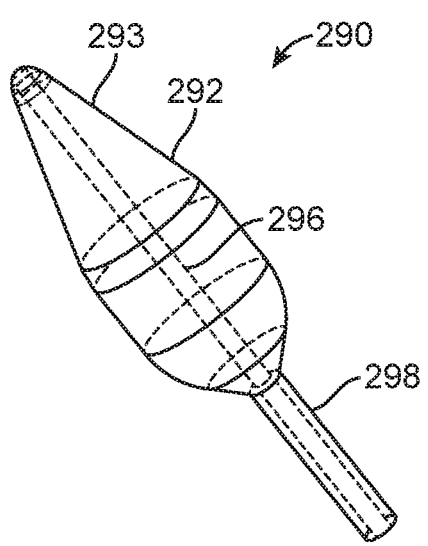
FIGS. 13A and 13B are perspective and side views, respectively, of a distal portion of a kidney stone removal system having a balloon, according to one embodiment.
Figure 13B:
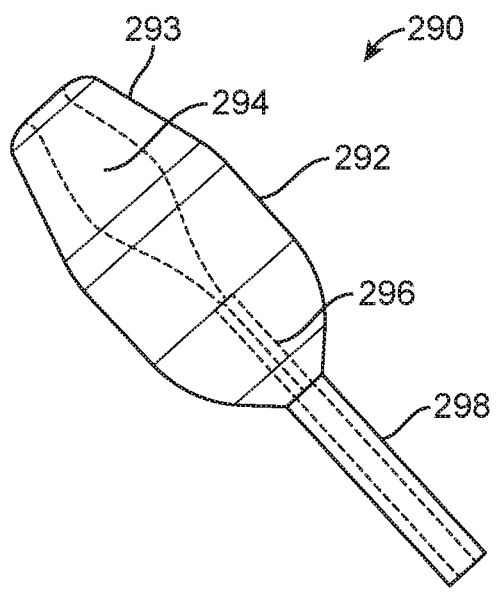

Referring now to FIGS. 13A and 13B, a distal portion of another alternative embodiment of a kidney stone removal device 290, including a protective balloon 292 is illustrated. Device 290 may include balloon 292, an outer shaft 298, and an inner shaft 296 that moves in and out of shaft 298. Balloon 292 may include a distal tapered portion 293 and an inner, stone entrapment space 294. When inner shaft 296 is fully advanced, stone entrapment space 294 is rolled outwards and becomes tapered portion 293 (as in FIG. 13A). When inner shaft 296 is pulled back/retracted proximally, back into outer shaft 298, tapered portion 293 rolls inward (or "invaginates") to form stone entrapment space 294.

In one embodiment, a method for using device 290 may involve advancing the distal end of device 290 into the ureter to a position near a kidney stone. Balloon 292 may then be partially inflated and then advanced around the obstruction from the direction of approach of device 290, such that the kidney stone becomes trapped in entrapment space 294. Balloon 292 may then optionally be inflated further, using any suitable inflation medium provided via a central lumen or specified inflation lumen(s) of shaft 298. This method of approaching and capturing the kidney stone is advantageous, because it eliminates the complexity of manipulating the device past the obstruction. This embodiment of device 290 may also reduce body lumen trauma and friction that results from the catheter lumen placement adjacent to the stone. Balloon 292 (or other complaint material member in alternative embodiments) will typically have a tapered shape and thickness configured to facilitate enveloping the stone without necking or forcing the stone out of balloon 292 during deployment. In various embodiments, for example, balloon 292 may include a tapered portion at its distal end with an angle of between about 2 degrees and about 45 degrees.

FIG. 13A shows device 290 with inner shaft 296 extended out of shaft 298 to its maximum extent. FIG. 13B shows inner shaft 296 retracted to pull back on the distal end of balloon 292, thus forming entrapment space 294. In some embodiments, balloon 292 may be rolled over a stone or other obstruction by retracting inner shaft 296 and advancing outer shaft 298. Alternatively, it may be possible to achieve the same or similar effect by only retracting inner shaft 296 or only advancing outer shaft 298. Whichever method is used, entrapment space 294 may be formed to entrap the kidney stone for removal.

Figure 14A:
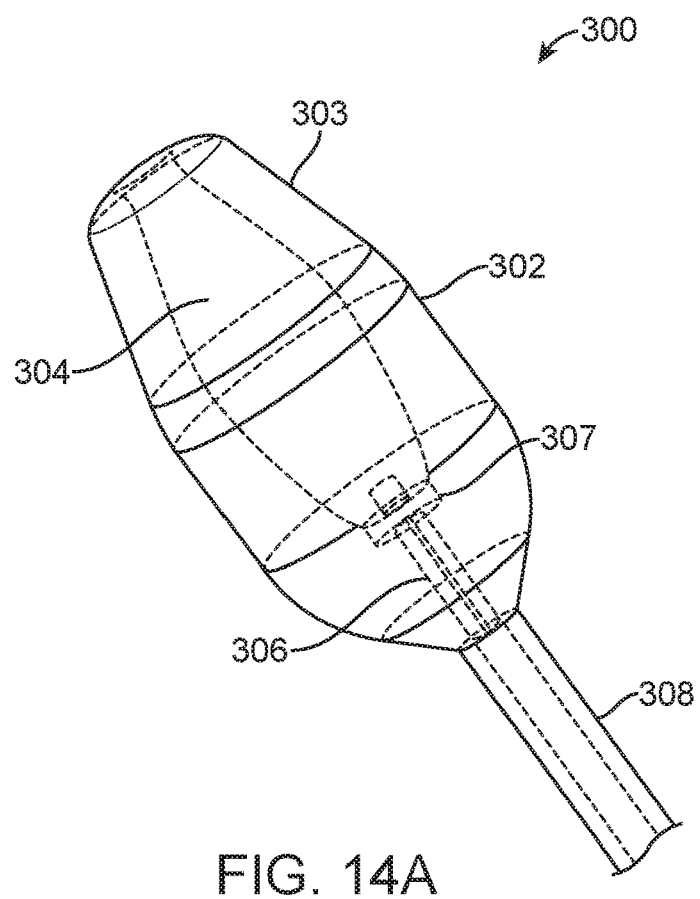
FIG. 14A is a perspective view of a distal portion of a kidney stone removal system having a balloon, according to an alternative embodiment.

With reference now to FIG. 14A, in an alternative embodiment, a kidney stone removal device 300 may include a balloon 302, an outer shaft 308, and an inner shaft 306 that moves in and out of shaft 308. Balloon 302 may include an inner, stone entrapment space 304 and a distal, tapered portion 303. Inner shaft 306 may include a rigid, distal ring 307 or platform, which connects shaft 306 to the inside edge of a slightly inverted balloon 302. The outside of balloon 302, attached to movable inner shaft 306, can be extended around the kidney stone or other obstruction. Ring 307 may be positioned to sit on the bottom of the stone/obstruction, and balloon 302 may be advanced around the stone to enclose the stone in entrapment space 304. Ring 307 may help prevent the bottom portion of the inverted balloon 302 from "necking down," which may help facilitate obstruction entrapment by balloon 302. The phenomenon of "necking down" refers to the narrowing of balloon 302 in the area where it connects to shaft 66, which can be seen in FIG. 13B.

Figure 14B:
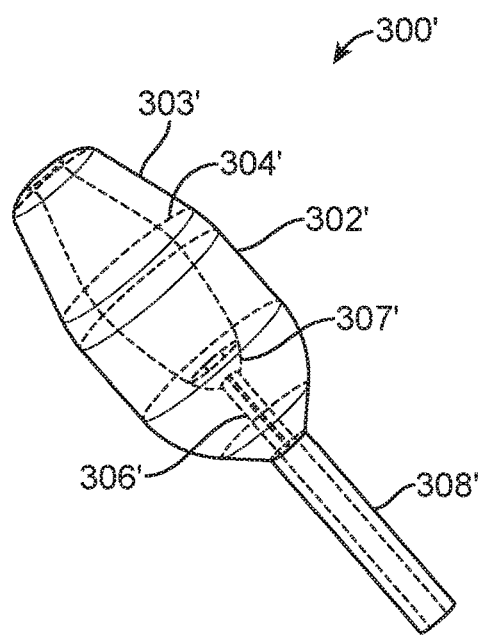
FIG. 14B is a perspective view of a distal portion of a kidney stone removal system having a balloon, according to another alternative embodiment.

With reference now to FIG. 14B, an alternative embodiment of a stone removal device 300' with a differently shaped ring 307' is illustrated. In all other ways, device 300' is the same as shown in FIG. 14A and includes a balloon 302' with a tapered portion 303' and an inner space 304', an outer shaft 308', and an inner shaft 306' that moves in and out of shaft 308'. In this embodiment, ring 307' may have an atraumatic configuration so that when inner shaft 306' is fully advanced, ring 307' will not inadvertently damage other structures. In one embodiment, a tapered complaint material could be attached to the tip of balloon 302' to increase the rigidity of the tip section relative to balloon 302'. This tapered section will provide additionally rigidity to the tip, and can prevent balloon 302' from necking down to a small diameter as it is deployed over the obstruction, similar to the function of ring 307' at its attachment with balloon 302'. This material may also serve as an atraumatic trip during catheter deployment, and may be superior in the case of tapered balloon 302', as it will conform to the balloon shape.

In any of the above-described embodiments, suction force may be used to help draw a kidney stone or other obstruction into the entrapment space in the balloon. In some embodiments, suction force may be applied via a central lumen in the inner shaft of the obstruction removal device, so that the suction force is applied directly inside the entrapment space of the balloon.

It is possible to combine any of the above-described removal methods. A combination of the above may be preferable in some embodiments, depending on the obstruction location, size, required retention force and/or other factors.

In all the embodiments described above in relation to FIGS. 13A, 13B, 14A and 14B, the retention member, namely the balloon, also acts as the wall protection member. The two-sided complaint material, which is described above as a balloon but which may have other configurations in alternative embodiments, may be partially infused with air, water, saline, a biocompatible lubricant, or a local anesthetic (such as lidocaine) then rolled or linearly extended past the stone. In some embodiments, as mentioned above, the dilation balloon may be perforated to allow at least some of the fluid to pass into the region around the obstruction. For example, a local anesthetic may be used to numb the region around the obstruction, a lubricant may be desired to reduce the friction of the obstruction on the surrounding wall, or the fluid may be used to provide a hydrodilation force around the balloon to reduce friction and/or tissue trauma.

Any of the embodiments described above in relation to FIGS. 13A, 13B, 14A and 14B may also include some form of visualization component. In some embodiments, for example, a visualization device may extend through a central lumen of the moveable inner shaft, thus providing visualization into the entrapment space of the balloon. In a 6 F catheter, a typical size deployed through the working channel of an endoscope, this inner lumen could be upwards of 1 mm (3 F). This would allow both a light source and fiber camera to be deployed down the central lumen for visualization.

Although this invention has been disclosed in the context of certain embodiments and examples, the present invention extends beyond the specifically disclosed embodiments to other alternative embodiments and/or uses of the invention and modifications and equivalents thereof. Thus, the foregoing description should not be interpreted as limiting the scope of the present invention as described by the following claims.

What is claimed is:

1. A device for removing a kidney stone from a urinary tract in a human or animal subject, the device comprising:
    a handle;
    a retention member slider coupled with the handle;
    an elongate, flexible, outer shaft having a distal end and a proximal end, wherein the outer shaft defines a longitudinal axis extending between the distal and proximal ends;
    a lumen wall protection member shaft coaxially disposed within the outer shaft;
    an inflatable balloon, comprising:
        a proximal attachment portion coupled with the distal end of the outer shaft;
        a proximal tapered portion immediately adjacent the proximal attachment portion, having a first longitudinal length, measured along the longitudinal axis;
        a central cylindrical portion immediately adjacent the proximal tapered portion, having a second longitudinal length, measured along the longitudinal axis;
        a distal tapered portion immediately adjacent the central cylindrical portion, having a third longitudinal length, measured along the longitudinal axis; and
        a distal attachment portion immediately adjacent the distal tapered portion, coupled with a distal end of the lumen wall protection member shaft,
        wherein the second longitudinal length is longer than the first longitudinal length, and the first longitudinal length is longer than the third longitudinal length;
    at least one eversion feature configured to facilitate preferential eversion of the distal tapered portion of the inflatable balloon into an inside of the balloon, rather than the proximal tapered portion, wherein the at least one eversion feature comprises a greater thickness of material on the proximal tapered portion as compared to the distal tapered portion; and
    an expandable obstruction retention member extending coaxially within the lumen wall protection member shaft and attached proximally to the retention member slider.

2. A device as in claim 1, wherein the distal tapered portion has a taper angle of between 30 degrees and 90 degrees.

3. A device as in claim 2, wherein the proximal tapered portion has a taper angle of between 5 degrees and 25 degrees.

4. A device as in claim 1, wherein the at least one eversion feature further comprises a higher durometer material on the proximal tapered portion as compared to the distal tapered portion.

5. A device as in claim 1, wherein the at least one eversion feature further comprises at least one extra layer of material on the proximal tapered portion as compared to the distal tapered portion.

6. A device as in claim 1, wherein the at least one eversion feature further comprises multiple support ribs on the proximal tapered portion.

7. A device as in claim 1, wherein the at least one eversion feature further comprises multiple surface features on the outer shaft at a location where the proximal attachment portion of the balloon is attached to the outer shaft.

8. A device as in claim 1, wherein the at least one eversion feature further comprises multiple surface features on the lumen wall protection member shaft at a location where the distal attachment portion of the balloon is attached to the lumen wall protection member shaft.

9. A device as in claim 1, wherein the balloon is configured to automatically deflate at least partially, and the distal tapered portion is configured to automatically evert into the inside of the balloon, when the kidney stone is pulled into the distal tapered portion or the balloon is advanced over the kidney stone.

10. A device as in claim 1, wherein a space between the outer shaft and the lumen wall protection member shaft comprises an inflation lumen in fluid communication with the inflatable balloon.

11. A device as in claim 1, wherein the lumen wall protection member shaft is movable along the longitudinal axis relative to the outer shaft, and wherein sliding the lumen wall protection member shaft proximally relative to the outer shaft causes the distal tapered portion to evert into the balloon.

12. A device as in claim 1, wherein the obstruction retention member comprises:
    a retention member shaft having a proximal end fixedly attached to the retention member slider, such that when the retention member slider slides back and forth along the handle, the retention member shaft slides with the retention member slider; and
    an expandable basket disposed at a distal end of the retention member shaft.

13. A device as in claim 12, further comprising an elongate, flexible, inner shaft extending coaxially within at least part of the lumen wall protection member shaft, wherein the obstruction retention member is disposed coaxially within the inner shaft.

14. A device as in claim 13, further comprising an elongate, flexible camera positioned coaxially within a lumen of the retention member shaft, wherein a proximal end of the camera is fixedly attached to the handle, such that the camera does not move relative to the handle and the inner shaft, and such that a distal end of the camera is located at or near a distal end of the inner shaft, wherein the retention member shaft slides back and forth between the inner shaft and the camera.

* * * * *